(12) United States Patent
Tilly et al.

(10) Patent No.: US 11,141,609 B2
(45) Date of Patent: Oct. 12, 2021

(54) DOSE GUIDED REAL-TIME ADAPTIVE RADIOTHERAPY

(71) Applicant: Elekta AB (publ), Stockholm (SE)

(72) Inventors: David Andreas Tilly, Uppsala (SE); Stella Lucie Riad, Sundbyberg (SE); Peter Kimstrand, Uppsala (SE); Nina Terese Tilly, Uppsala (SE); Klas Mareks von Würtemberg, Stockholm (SE)

(73) Assignee: Elekta AB (publ), Stockholm (SE)

( * ) Notice: Subject to any disclaimer, the term of this patent is extended or adjusted under 35 U.S.C. 154(b) by 230 days.

(21) Appl. No.: 16/413,555

(22) Filed: May 15, 2019

(65) Prior Publication Data

US 2020/0360731 A1 Nov. 19, 2020

(51) Int. Cl.
*A61N 5/10* (2006.01)
*G16H 20/40* (2018.01)

(52) U.S. Cl.
CPC ......... *A61N 5/1071* (2013.01); *A61N 5/1045* (2013.01); *A61N 5/1049* (2013.01);
(Continued)

(58) Field of Classification Search
CPC .. A61N 5/1031; A61N 5/1039; A61N 5/1045; A61N 5/1071; A61N 2005/1062;
(Continued)

(56) References Cited

U.S. PATENT DOCUMENTS 6,128,366 A * 10/2000 Siochi .................. A61N 5/1031
378/65
6,240,161 B1 5/2001 Siochi
(Continued)

FOREIGN PATENT DOCUMENTS

WO 2018048575 3/2018

OTHER PUBLICATIONS

Crijns, S. P. M., et al., "Proof of concept of MRI-guided tracked radiation delivery: tracking one-dimensional motion", Physics in Medicine & Biology 57.23, (Nov. 14, 2012), 7863-7872.
(Continued)

*Primary Examiner* — Chih-Cheng Kao
(74) *Attorney, Agent, or Firm* — Schwegman Lunberg & Woessner, P.A.; Sanjay Agrawal

(57) ABSTRACT

Techniques for adjusting radiotherapy treatment for a patient in real-time are provided. The techniques include determining a patient anatomy at a first time within a given radiotherapy treatment fraction after a radiotherapy treatment dose has been delivered by a radiotherapy device; retrieving a reference patient anatomy for the given radiotherapy treatment fraction that indicates a prescribed dose parameter to be delivered within the given radiotherapy treatment fraction; comparing the patient anatomy at the first time with the reference patient anatomy during the given radiotherapy treatment fraction; and based on the comparison of the patient anatomy at the first time with the reference patient anatomy, adjusting a parameter of the radiotherapy device to change an amount of radiotherapy treatment dose delivered at a second time, following the first time, within the given radiotherapy treatment fraction in accordance with the prescribed dose parameter to be delivered within the given radiotherapy treatment fraction.

28 Claims, 6 Drawing Sheets

(52) U.S. Cl.
CPC .......... *A61N 5/1067* (2013.01); *A61N 5/1031* (2013.01); *A61N 5/1039* (2013.01); *A61N 2005/1087* (2013.01); *G16H 20/40* (2018.01)

(58) Field of Classification Search
CPC .. A61N 5/1038; A61N 5/1042; A61N 5/1049; A61N 5/1067
See application file for complete search history.

(56) References Cited

U.S. PATENT DOCUMENTS

| | | | |
|---|---|---|---|
| 6,882,702 | B2 | 4/2005 | Luo |
| 7,469,035 | B2 | 12/2008 | Keall et al. |
| 7,505,559 | B2 | 3/2009 | Kuduvalli |
| 7,513,861 | B2 | 4/2009 | Klein et al. |
| 7,639,853 | B2 | 12/2009 | Olivera et al. |
| 7,907,987 | B2 | 3/2011 | Dempsey |
| 8,095,203 | B2 | 1/2012 | Wright et al. |
| 8,222,616 | B2 | 7/2012 | Lu et al. |
| 8,509,383 | B2 | 8/2013 | Lu et al. |
| 8,848,869 | B2 | 9/2014 | Gertner et al. |
| 9,192,786 | B2 | 11/2015 | Yan et al. |
| 9,314,160 | B2 | 4/2016 | Adler, Jr. et al. |
| 9,468,776 | B2 | 10/2016 | Fredriksson |
| 9,652,871 | B2 | 5/2017 | Han et al. |
| 9,950,192 | B2 | 4/2018 | Wu et al. |
| 10,092,774 | B1 | 10/2018 | Vanderstraten et al. |
| 2006/0241332 | A1* | 10/2006 | Klein ................... A61N 5/1015 600/1 |
| 2008/0031406 | A1 | 2/2008 | Yan et al. |
| 2008/0159478 | A1 | 7/2008 | Keall et al. |
| 2009/0110145 | A1 | 4/2009 | Lu et al. |
| 2010/0150309 | A1 | 6/2010 | Nord et al. |
| 2010/0322381 | A1* | 12/2010 | Stahl ..................... A61N 5/1042 378/65 |
| 2012/0069962 | A1 | 3/2012 | Fallone et al. |
| 2012/0123184 | A1 | 5/2012 | Otto et al. |
| 2015/0065777 | A1 | 3/2015 | Darwish |
| 2015/0306423 | A1 | 10/2015 | Bharat et al. |
| 2018/0235554 | A1 | 8/2018 | Burgett |
| 2018/0369611 | A1* | 12/2018 | Owens ................. A61N 5/1049 |
| 2019/0015683 | A1 | 1/2019 | Vinh-hung et al. |
| 2019/0054315 | A1 | 2/2019 | Isola et al. |
| 2019/0143145 | A1* | 5/2019 | Laurence, Jr. ......... A61B 34/10 600/1 |
| 2020/0105399 | A1* | 4/2020 | Laaksonen ............... G06N 3/08 |

OTHER PUBLICATIONS

Kontaxis, C., et al., "Towards adaptive IMRT sequencing for the MR-linac", Physics in Medicine & Biology 60.6, (Mar. 6, 2015), 2493-2509.

Moore, Douglas, et al., "Fast leaf-fitting with generalized underdose/overdose constraints for real-time MLC tracking", Med. Phys. 43 (1), Jan. 2016; 465-474, (Dec. 31, 2015), 10 pgs.

Ramakrishnan, Jagdish, et al., "A dynamic programming approach to adaptive fractionation", Physics in Medicine & Biology 57.5, (Feb. 14, 2012), 1203-1216.

Tacke, Martin, et al., "Real-time tumor tracking: Automatic compensation of target motion using the Siemens 160 MLC", Medical physics 37.2, (Jan. 25, 2010), 753-761.

Tilly, David, et al., "Fast dose algorithm for generation of dose coverage probability for robustness analysis of fractionated radiotherapy", Physics in Medicine & Biology 60.14, (Jun. 29, 2015), 5439-5454.

Tilly, David, "Probabilistic treatment planning based on dose coverage: How to quantify and minimize the effects of geometric uncertainties in radiotherapy", Diss. Acta Universitatis Upsaliensis, (2016), 128 pgs.

Tyagi, N, "A real time dose monitoring and dose reconstruction tool for patient specific VMAT QA and delivery.", Med Phys 39(12), (Dec. 2012), 2 pgs.

Wisotzky, Eric, et al., "A novel leaf sequencing optimization algorithm which considers previous underdose and overdose events for MLC tracking radiotherapy", Medical physics 43.1, (Dec. 22, 2015), 132-136.

Ziegenhein, Peter, et al., "Real-time energy/mass transfer mapping for online 4D dose reconstruction", Scientific Reports 8:3662, (Feb. 26, 2018), 10 pgs.

"International Application Serial No. PCT EP2020 063199, International Search Report dated Jun. 22, 2020", 6 pgs.

"International Application Serial No. PCT EP2020 063199, Written Opinion dated Jun. 22, 2020", 9 pgs.

Keall, P J, "Motion adaptive x-ray therapy: a feasibility study", Phys. Med. Biol. 46, (2001), 10 pgs.

* cited by examiner

DOSE GUIDED REAL-TIME ADAPTIVE RADIOTHERAPY

TECHNICAL FIELD

This disclosure relates generally to radiation therapy or radiotherapy. More specifically, this disclosure relates to systems and methods for adjusting parameters of a radiotherapy device during radiotherapy treatment.

BACKGROUND

Radiotherapy is used to treat cancers and other ailments in mammalian (e.g., human and animal) tissue. Radiotherapy include linear particle accelerator (LINAC) based radiotherapy and circular particle accelerators (e.g., cyclotron, synchrotron, and synchrocyclotron). Such particle accelerators accelerate charged subatomic particles or ions to a high speed by subjecting them to a series of oscillating electric potentials along an external linear beamline. Protons and heavier ions such as carbon ions are all accelerated in circular accelerators. The direction and shape of the radiation beam should be accurately controlled to ensure the tumor receives the prescribed radiation, and the placement of the beam should be such as to minimize damage to the surrounding healthy tissue including especially sensitive organs, often called the organ(s) at risk (OARs). Treatment planning can be used to control radiation beam parameters, and a radiotherapy device effectuates a treatment by delivering a spatially varying dose distribution to the patient according to a treatment plan.

OVERVIEW

In some embodiments, a computer-implemented method, non-transitory computer-readable medium, and a system comprising a memory and processor are provided for adjusting radiotherapy treatment for a patient in real-time. The method, computer-readable medium storing instructions, and processor execute operations, including determining a patient anatomy at a first time within a given radiotherapy treatment fraction after a radiotherapy treatment dose has been delivered by a radiotherapy device; retrieving a reference patient anatomy for the given radiotherapy treatment fraction that indicates a prescribed dose parameter to be delivered within the given radiotherapy treatment fraction; comparing the patient anatomy at the first time with the reference patient anatomy during the given radiotherapy treatment fraction; and based on the comparison of the patient anatomy at the first time with the reference patient anatomy, adjusting a parameter of the radiotherapy device to change an amount of radiotherapy treatment dose delivered at a second time, following the first time, within the given radiotherapy treatment fraction in accordance with the prescribed dose parameter to be delivered within the given radiotherapy treatment fraction.

In some embodiments, the parameter of the radiotherapy device is adjusted while maintaining the prescribed dose parameter to be delivered within the given radiotherapy treatment fraction, wherein the prescribed dose parameter comprises at least one of a prescribed fraction dose to be delivered to a target within the given radiotherapy treatment fraction, a maximum dose delivered to an organ at risk within the given radiotherapy treatment fraction, or a maximum dose delivered to a relative volume of the organ at risk, further comprising adjusting the parameter of the radiotherapy device throughout the given radiotherapy treatment fraction such that an aggregate amount of radiotherapy treatment dose delivered at multiple times within the given radiotherapy treatment fraction corresponds to the prescribed dose parameter.

In some embodiments, the method, computer-readable medium storing instructions, and processor execute operations, including determining a first amount of overlap between a tumor in the patient and an organ at risk, laterally or in depth, based on the determined patient anatomy at the first time, the first amount of overlap indicating a first quantity of radiation exposure to the tumor relative to the organ at risk; and determining a reference amount of overlap between the tumor in the patient and the organ at risk laterally or in depth based on the reference patient anatomy, the reference amount of overlap indicating a reference quantity of radiation exposure to the tumor relative to the organ at risk. In some implementations, the method, computer-readable medium storing instructions, and processor execute operations, including determining that the first amount is less than the reference amount; and increasing the amount of radiotherapy treatment dose delivered at the second time in response to determining that the first amount is less than the reference amount.

In some implementations, the method, computer-readable medium storing instructions, and processor execute operations, including determining that the first amount is greater than the reference amount; and decreasing the amount of radiotherapy treatment dose delivered at the second time in response to determining that the first amount is greater than the reference amount. In some implementations, the method, computer-readable medium storing instructions, and processor execute operations, including determining a relationship (e.g., a ratio) between the first amount to the reference amount; and modifying the amount of radiotherapy treatment dose delivered at the second time as a linear or quadratic function of the relationship (e.g., the ratio) between the first amount to the reference amount.

In some embodiments, the method, computer-readable medium storing instructions, and processor execute operations, including determining a first distance between a border of a tumor in the patient and an organ at risk based on the determined patient anatomy at the first time; determining a second distance between the border the tumor in the patient and the organ at risk based on the reference patient anatomy; and increasing the amount of radiotherapy treatment dose delivered at the second time based on a deviation between the first and second distances. In some embodiments, the method, computer-readable medium storing instructions, and processor execute operations, including determining a first distance between a border of a tumor in the patient and an organ at risk based on the determined patient anatomy at the first time; determining a second distance between the border the tumor in the patient and the organ at risk based on the reference patient anatomy; and decreasing the amount of radiotherapy treatment dose delivered at the second time based on a deviation between the first and second distances.

In some embodiments, the parameter of the radiotherapy device comprises a dose amount in a given time or a gantry rotation speed, and the method, computer-readable medium storing instructions, and processor execute operations, including generating a dose amount per time factor as a function of a dose amount per time parameter and amount of overlap parameter; and adjusting the dose amount or the gantry rotation speed by the dose amount per time factor. In some implementations, a result of the comparison of the patient anatomy at the first time is compared with the reference patient anatomy with the amount of overlap parameter, the dose amount is increased when the result is greater than the amount of overlap parameter, and wherein the dose is decreased when the result is less than the amount of overlap parameter.

In some implementations, the dose amount per time factor and the amount of overlap parameters are optimized during planning before starting the given radiotherapy treatment fraction or during the given radiotherapy treatment fraction. In some implementations, the dose amount per time parameter and the amount of overlap parameters are computed, using a machine learning technique, based on a plurality of radiotherapy treatment simulations. In some implementations, at least one of multi-leaf collimator (MLC) setting, a jaw collimator setting, the dose amount per time parameter or the amount of overlap parameter is computed based on solving an optimization problem that balances amount of radiotherapy dose delivery to a tumor and at least one of the amount of radiotherapy dose delivery to one or more organ(s) at risk or the amount of radiotherapy dose delivery to healthy tissue.

In some embodiments, the parameter comprises a multi-leaf collimator (MLC) setting and a jaw collimator setting, and the method, computer-readable medium storing instructions, and processor execute operations, including generating an collimator adjustment amount based on an overlap amount computed as a function of an amount of sparing of dose delivery to normal tissue relative to a dose delivered to a target; and adjusting the MLC and jaw setting of the radiotherapy device by the collimator adjustment amount. In some implementations adjusting the collimator setting comprises modifying positions of the jaws and the leaves of the MLC to change a shape of the collimator opening, the positions being modified based on the collimator adjustment amount, wherein a position of one of the leaves of the MLC is adjusted by a different amount than a position of another one of the leaves of the MLC.

In some embodiments, the method, computer-readable medium storing instructions, and processor execute operations, including computing a level of accuracy of the determined patient anatomy at the first time; and modifying the radiotherapy device parameter based on the computed level of accuracy. In some embodiments, the method, computer-readable medium storing instructions, and processor execute operations, including estimating an amount of dose that remains to be delivered within the given radiotherapy treatment fraction, wherein the parameter of the radiotherapy device is adjusted based on the estimated amount of dose that remains to be delivered.

In some embodiments, the radiotherapy treatment dose is delivered to a given region in the patient anatomy at the first time, and the method, computer-readable medium storing instructions, and processor execute operations, including determining whether the given region in the patient anatomy will be irradiated by the radiotherapy device at another time within the given radiotherapy treatment fraction; and modifying the amount of radiotherapy treatment dose delivered at the second time as a function of the determination of whether the given region in the patient anatomy will be irradiated by the radiotherapy device at another time within the given radiotherapy treatment fraction. The method, computer-readable medium storing instructions, and processor execute operations, including modifying the amount based on whether the another time is closer to a start of the given radiotherapy treatment fraction or an end of the given radiotherapy treatment fraction.

In some embodiments, the method, computer-readable medium storing instructions, and processor execute operations, including re-ordering segments in a radiotherapy treatment plan to change times when different regions of the patient anatomy are irradiated within the given radiotherapy treatment fraction. The radiotherapy treatment plan identifies a first region of the patient anatomy to irradiate at a third time within the given radiotherapy treatment fraction and a second region of the patient anatomy to irradiate at a fourth time within the given radiotherapy treatment fraction; and after re-ordering the segments, the radiotherapy device irradiates the first region of the patient anatomy at the fourth time within the given radiotherapy treatment fraction and the second region of the patient anatomy at the third time within the given radiotherapy treatment fraction. The method, computer-readable medium storing instructions, and processor execute operations, including adding one or more segments in a radiotherapy treatment plan to perform re-scanning and increase times when one or more regions of the patient anatomy are irradiated within the given radiotherapy treatment fraction or to irradiate regions of the patient anatomy that are additional and different from regions specified to be irradiated in the radiotherapy treatment plan.

In some embodiments, the method, computer-readable medium storing instructions, and processor execute operations, including computing an uncertainty associated with determining the patient anatomy at the first time; and modifying the radiotherapy device parameter based on the computed uncertainty.

The above overview is intended to provide an overview of subject matter of the present patent application. It is not intended to provide an exclusive or exhaustive explanation of the inventive subject matter. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
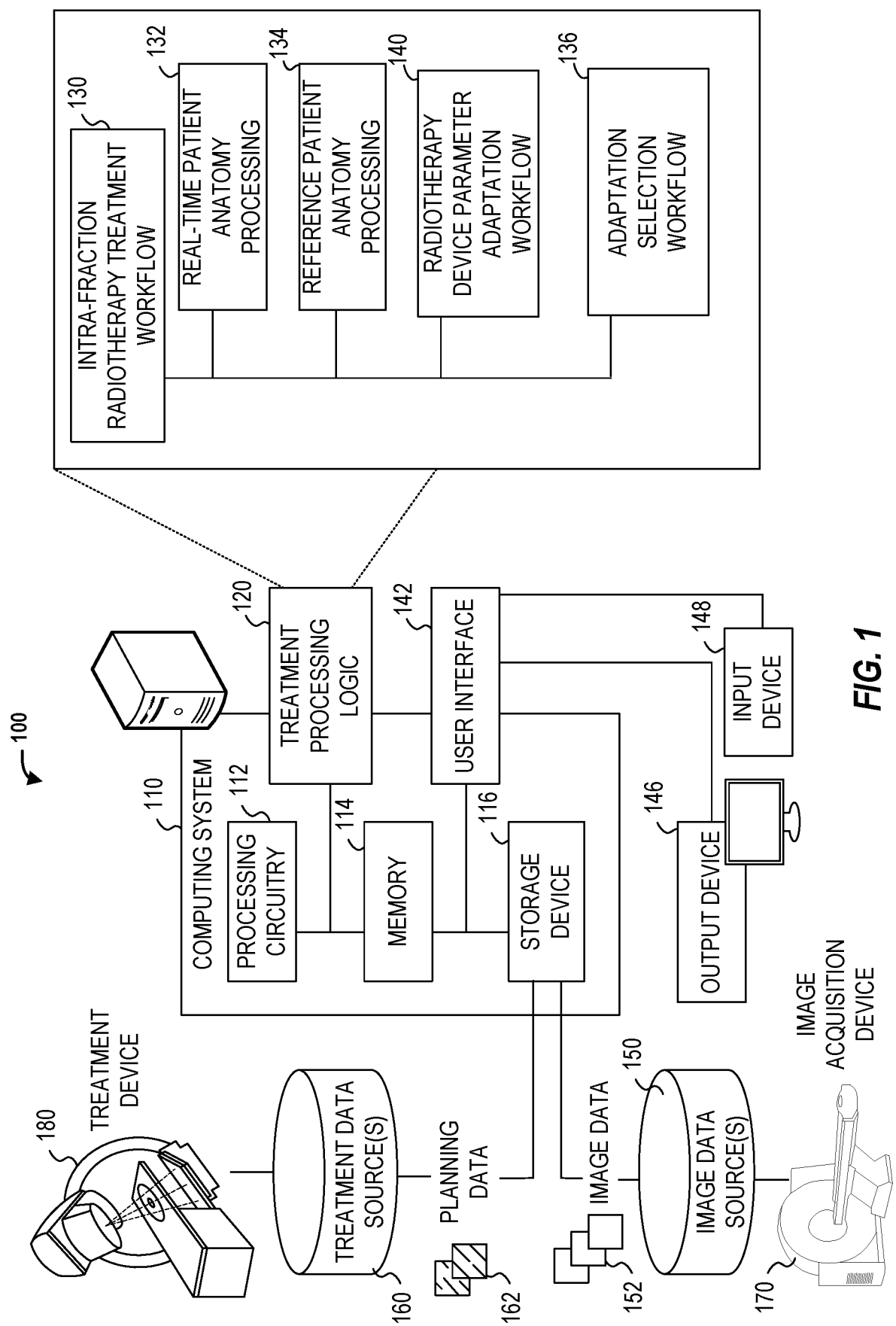
FIG. 1 illustrates an exemplary radiotherapy system adapted for performing intra-fraction radiotherapy treatment according to some examples

The present disclosure includes various techniques to improve and enhance radiotherapy treatment by adjusting radiotherapy device parameters in real-time within a given treatment fraction. The technical benefits include reduced radiotherapy treatment time and may result in many apparent medical treatment benefits (including improved accuracy of radiotherapy treatment, reduced exposure to unintended radiation, and the like). The disclosed techniques may be applicable to a variety of medical treatment and diagnostic settings or radiotherapy treatment equipment and devices.

The present disclosure is about adjusting radiotherapy device parameters in real time within a given fraction of radiotherapy treatment in a way that maintains a prescribed dose specified in a treatment plan. A radiation therapy treatment fraction is a fraction of the entire prescribed radiation dose. For example, a radiation therapy treatment might consist of 30 separate fractions, one fraction a day over the course of a month. In this regard, each radiation therapy fraction can be based on an updated radiation therapy plan, as described below.

Prior approaches modify treatment plan parameters and radiotherapy device parameters between treatment fractions. Specifically, according to the prior approaches, after a given treatment fraction is completed, treatment information is analysed to make various modifications for application to a subsequent treatment fraction, which could take place days or weeks later. Some prior approaches generally adjust parameters of a radiotherapy device based on tracking patient motion in real-time. However, such approaches adjust the parameters without considering the total influence of the radiation across the entire treatment fraction (e.g., how much radiation is delivered to the target or an OAR during the entire treatment fraction based on such general adjustments) and end up over- or under-delivering radiation to the tumor and/or exceeding the dose allowed to an OAR. In order to optimize radiotherapy dose delivery to a target (e.g., a tumor) or reduce the amount of radiation delivered to an OAR, rather than waiting several days or weeks or generally adjusting parameters based on patient motion, the disclosed techniques perform modifications to the radiotherapy device parameters during the same fraction (i.e., intra-fraction) while maintaining a target dose according to a prescription.

In order to perform real-time intra-fraction adjustments to the radiotherapy device parameters, the disclosed techniques determine a patient anatomy at a first time within a given radiotherapy treatment fraction after a radiotherapy treatment dose has been delivered by a radiotherapy device. A reference patient anatomy for the given radiotherapy treatment fraction is retrieved that indicates a prescribed dose parameter to be delivered within the given radiotherapy treatment fraction. The patient anatomy at the first time is compared with the reference patient anatomy during the given radiotherapy treatment fraction. Based on how the current patient anatomy at the first time compares with the reference (or expected) patient anatomy at the first time, one or several parameter(s) of the radiotherapy device is adjusted. In some embodiments, the parameters are adjusted based on a function that specifies whether to increase or decrease the subsequent dose to be delivered at a second time within the given fraction and the amount by which to increase or decrease the subsequent dose. In this way, the parameters of the radiotherapy device are adjusted to change an amount of radiotherapy treatment dose delivered at a second time, following the first time, within the given radiotherapy treatment fraction while maintaining the prescribed dose parameter to be delivered within the given radiotherapy treatment fraction.

Specifically, the prescribed dose parameter includes at least one of a prescribed fraction dose to be delivered within the given radiotherapy treatment fraction or a maximum dose delivered to an OAR within the given radiotherapy treatment fraction and the parameter of the device is adjusted throughout the given radiotherapy treatment fraction such that an aggregate amount of radiotherapy treatment dose delivered at multiple times within the given radiotherapy treatment fraction corresponds to the prescribed dose parameter. The maximum dose delivered to the OAR may represent dose to a small volume (e.g. the dose that 2% of the OAR receives). Namely, the maximum dose delivered to the OAR may be a function of the size or volume of the OAR and the relative maximum percentage of the size or volume of the OAR that receives the dose. For example, an amount of dose that remains to be delivered within the given radiotherapy treatment fraction is estimated and the parameter of the radiotherapy device is adjusted based on the estimated amount of dose that remains to be delivered. A determination is made as to whether the given region in the patient anatomy, that has already been irradiated, will be irradiated by the radiotherapy device at another time within the given radiotherapy treatment fraction. The amount of radiotherapy treatment dose delivered at the second time or the another time is modified as a function of the determination of whether the given region in the patient anatomy will be irradiated by the radiotherapy device at another time within the given radiotherapy treatment fraction. In particular, if it is determined that the given region will be irradiated again during the same radiotherapy treatment fraction, then the amount of radiotherapy treatment dose delivered at a subsequent time is reduced but, if it is determined that the given region will not be irradiated again during the same radiotherapy treatment fraction, then the amount of radiotherapy treatment dose delivered at a subsequent time is increased.

As an example, the intra-fraction dose can change as a function of the geometrical advantage of the dose delivered at a subsequent time within a given fraction. Namely, if the geometry is more advantageous than compared to the geometry indicated in the reference treatment plan, then more or less dose is delivered from the current direction, current segment, current part, sub-treatment, or sub-fraction of the treatment. Namely, at a given angle, the geometry could first be more favourable and then less favourable which might result in more or less dose from that direction as compared to the treatment plan. Specifically, if the amount of overlap between the OAR and the target at the current time within the given fraction is less than the amount of overlap expected for the current time in the treatment plan, then more dose is delivered at the next intra-fraction time than specified in the treatment plan. As another example, if the distance between the OAR and the target at the current time within the given fraction is greater than the distance expected for the current time in the treatment plan, then more dose is delivered at the next intra-fraction time than specified in the treatment plan. The amount by which the dose is increased may depend on the total dose specified to be delivered in the treatment plan for the given fraction. As such, if the dose is increased by a first amount at a given time within the treatment fraction, then the dose is decreased by a total amount equal to the first amount in subsequent dose delivery within the treatment fraction following the given time. This ensures that the total amount of radiotherapy dose prescribed in the treatment plan is maintained even though the dose is increased beyond what is specified for a given time in the treatment fraction in the treatment plan. In some embodiments, if the dose delivered at a given time in the treatment fraction exceeds the planned dose in the treatment plan, the treatment is aborted.

FIG. 1 illustrates an exemplary radiotherapy system 100 adapted to perform radiotherapy plan processing operations using one or more of the approaches discussed herein. These radiotherapy plan processing operations are performed to enable the radiotherapy system 100 to provide radiation therapy to a patient based on specific aspects of captured medical imaging data and therapy dose calculations or radiotherapy machine configuration parameters. Specifically, the following processing operations may be implemented as part of an intra-fraction radiotherapy treatment workflow 130 and a radiotherapy device parameter adaptation workflow 140, implemented by treatment processing logic 120. It will be understood, however, that many variations and use cases of the following trained models and treatment processing logic 120 may be provided, including in data verification, visualization, and other medical evaluative and diagnostic settings.

The radiotherapy system 100 includes a radiotherapy processing computing system 110 which hosts treatment processing logic 120. The radiotherapy processing computing system 110 may be connected to a network (not shown), and such network may be connected to the Internet. For instance, a network can connect the radiotherapy processing computing system 110 with one or more medical information sources (e.g., a radiology information system (RIS), a medical record system (e.g., an electronic medical record (EMR)/electronic health record (EHR) system), an oncology information system (OIS)), one or more image data sources 150, an image acquisition device 170 (e.g., an imaging modality), a treatment device 180 (e.g., a radiation therapy device, also referred to herein as a radiotherapy device), and a treatment data source 160. As an example, the radiotherapy processing computing system 110 can be configured to monitor current patient geometry to calculate dose delivery to a subject (e.g., from one or more MR images) within a given fraction in real time and modify parameters of the radiotherapy device for subsequent doses delivered in the same fraction based on a comparison of the calculated dose delivery to an expected dose delivery specified in a treatment plan by executing instructions or data from the treatment processing logic 120.

The radiotherapy processing computing system 110 may include processing circuitry 112, memory 114, a storage device 116, and other hardware and software-operable features such as a user interface 142, a communication interface (not shown), and the like. The storage device 116 may store transitory or non-transitory computer-executable instructions, such as an operating system, radiation therapy treatment plans (e.g., training data, such as paired prior patient data, such as diagnosis, prescription, treatment planning strategies, and intra-fraction radiotherapy device adaptation strategies and device adjustment amounts, and the like), software programs (e.g., image processing software, image or anatomical visualization software, artificial intelligence (AI) or ML implementations and algorithms such as provided by deep learning models, ML models, and neural networks, etc.), and any other computer-executable instructions to be executed by the processing circuitry 112.

In an example, the processing circuitry 112 may include a processing device, such as one or more general-purpose processing devices such as a microprocessor, a central processing unit (CPU), a graphics processing unit (GPU), an accelerated processing unit (APU), or the like. More particularly, the processing circuitry 112 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processing circuitry 112 may also be implemented by one or more special-purpose processing devices such as an application-specific integrated circuit (ASIC), a field programmable gate array (FPGA), a digital signal processor (DSP), a System on a Chip (SoC), or the like.

As would be appreciated by those skilled in the art, in some examples, the processing circuitry 112 may be a special-purpose processor, rather than a general-purpose processor. The processing circuitry 112 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processing circuitry 112 may also include graphical processing units such as a GPU from the GeForce®, Quadro®, Tesla® family manufactured by Nvidia™, GMA, Iris™ family manufactured by Intel™, or the Radeon™ family manufactured by AMD™. The processing circuitry 112 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one physical (circuitry based) or software based processor, for example, a multi-core design or a plurality of processors each having a multi-core design. The processing circuitry 112 can execute sequences of transitory or non-transitory computer program instructions, stored in memory 114, and accessed from the storage device 116, to perform various operations, processes, methods that will be explained in greater detail below. It should be understood that any component in system 100 may be implemented separately and operate as an independent device and may be coupled to any other component in system 100 to perform the techniques described in this disclosure.

The memory 114 may comprise read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including images, training data, ML technique parameters, device adaptation functions, data, or transitory or non-transitory computer-executable instructions (e.g., stored in any format) capable of being accessed by the processing circuitry 112, or any other type of computer device. For instance, the computer program instructions can be accessed by the processing circuitry 112, read from the ROM, or any other suitable memory location, and loaded into the RAM for execution by the processing circuitry 112.

The storage device 116 may constitute a drive unit that includes a transitory or non-transitory machine-readable medium on which is stored one or more sets of transitory or non-transitory instructions and data structures (e.g., software) embodying or utilized by any one or more of the methodologies or functions described herein (including, in various examples, the treatment processing logic 120 and the user interface 142). The instructions may also reside, completely or at least partially, within the memory 114 and/or within the processing circuitry 112 during execution thereof by the radiotherapy processing computing system 110, with the memory 114 and the processing circuitry 112 also constituting transitory or non-transitory machine-readable media.

The memory 114 and the storage device 116 may constitute a non-transitory computer-readable medium. For example, the memory 114 and the storage device 116 may store or load transitory or non-transitory instructions for one or more software applications on the computer-readable medium. Software applications stored or loaded with the memory 114 and the storage device 116 may include, for example, an operating system for common computer systems as well as for software-controlled devices. The radiotherapy processing computing system 110 may also operate a variety of software programs comprising software code for implementing the treatment processing logic 120 and the user interface 142. Further, the memory 114 and the storage device 116 may store or load an entire software application, part of a software application, or code or data that is associated with a software application, which is executable by the processing circuitry 112. In a further example, the memory 114 and the storage device 116 may store, load, and manipulate one or more radiation therapy treatment plans, imaging data, segmentation data, treatment visualizations, histograms or measurements, AI model data (e.g., weights and parameters), training data, labels and mapping data, and the like. It is contemplated that software programs may be stored not only on the storage device 116 and the memory 114 but also on a removable computer medium, such as a hard drive, a computer disk, a CD-ROM, a DVD, a Blu-Ray DVD, USB flash drive, a SD card, a memory stick, or any other suitable medium; such software programs may also be communicated or received over a network.

Although not depicted, the radiotherapy processing computing system 110 may include a communication interface, network interface card, and communications circuitry. An example communication interface may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a IEEE 802.11/Wi-Fi adapter), a telecommunication adapter (e.g., to communicate with 3G, 4G/LTE, and 5G, networks and the like), and the like. Such a communication interface may include one or more digital and/or analog communication devices that permit a machine to communicate with other machines and devices, such as remotely located components, via a network. The network may provide the functionality of a local area network (LAN), a wireless network, a cloud computing environment (e.g., software as a service, platform as a service, infrastructure as a service, etc.), a client-server, a wide area network (WAN), and the like. For example, the network may be a LAN or a WAN that may include other systems (including additional image processing computing systems or image-based components associated with medical imaging or radiotherapy operations).

In an example, the radiotherapy processing computing system 110 may obtain image data 152 from the image data source 150 (e.g., MR images), for hosting on the storage device 116 and the memory 114. In yet another example, the software programs may substitute functions of the patient images such as signed distance functions or processed versions of the images that emphasize some aspect of the image information.

In an example, the radiotherapy processing computing system 110 may obtain or communicate image data 152 from or to image data source 150. In further examples, the treatment data source 160 receives or updates the planning data 162 as a result of radiotherapy device parameter adjustments generated by the intra-fraction radiotherapy treatment workflow 130; the image data source 150 may also provide or host the image data 152 for use in the intra-fraction radiotherapy treatment workflow 140.

The processing circuitry 112 may be communicatively coupled to the memory 114 and the storage device 116, and the processing circuitry 112 may be configured to execute computer-executable instructions stored thereon from either the memory 114 or the storage device 116. The processing circuitry 112 may execute instructions to cause medical images from the image data 152 to be received or obtained in memory 114 and processed using the treatment processing logic 120.

In addition, the processing circuitry 112 may utilize software programs to generate intermediate data such as updated parameters to be used, for example, by a neural network model, machine learning model, intra-fraction radiotherapy treatment workflow 130, or other aspects involved with generation of intra-fraction device parameter adjustments, as discussed herein. Further, such software programs may utilize the treatment processing logic 120 to implement the intra-fraction radiotherapy treatment workflow 130 to produce updated radiotherapy parameters to provide to the treatment data source 160 to modify a dose delivered to a target within a given fraction and/or for presentation on output device 146, using the techniques further discussed herein. The processing circuitry 112 may subsequently then transmit the updated radiotherapy parameters via a communication interface and the network to the treatment device 180, where the updated parameters will be used to treat a patient with radiation via the treatment device 180, consistent with results of the workflow 130. Other outputs and uses of the software programs and the workflow 130 may occur with use of the radiotherapy processing computing system 110. Radiotherapy parameters may include MLC positions and settings, gantry angle, radiation dose amount (e.g., amount of monitor units (MU), radiotherapy beam direction, radiation beam size, arc placement, beam on and off time duration, machine parameters, segments, gantry speed, MRI pulse sequence, any combination thereof, and so forth.

In the examples herein, the processing circuitry 112 may execute software programs that invoke the treatment processing logic 120 to implement functions of ML, deep learning, neural networks, generative machine learning model, a generative adversarial network, and other aspects of artificial intelligence for a device adaptation model (that specifies a device adaptation strategy and/or parameter adjustment amount) within a given fraction. For instance, the processing circuitry 112 may execute software programs that train, analyze, predict, evaluate, and generate a device adaptation model from a received treatment information of multiple patients.

In an example, the image data 152 may include one or more MRI image (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, 2D Cone beam CT, 3D CT, 3D CBCT, 4D CT, 4DCBCT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer-generated synthetic images (e.g., pseudo-CT images) and the like. Further, the image data 152 may also include or be associated with medical image processing data, for instance, training images, and ground truth images, contoured images, and dose images. In other examples, an equivalent representation of an anatomical area may be represented in non-image formats (e.g., coordinates, mappings, etc.).

In an example, the image data 152 may be received from the image acquisition device 170 and stored in one or more of the image data sources 150 (e.g., a Picture Archiving and Communication System (PACS), a Vendor Neutral Archive (VNA), a medical record or information system, a data warehouse, etc.). Accordingly, the image acquisition device 170 may comprise an MRI imaging device, a CT imaging device, a PET imaging device, an ultrasound imaging device, a fluoroscopic device, a SPECT imaging device, an integrated Linear Accelerator and MRI imaging device, CBCT imaging device, or other medical imaging devices for obtaining the medical images of the patient. The image data 152 may be received and stored in any type of data or any type of format (e.g., in a Digital Imaging and Communications in Medicine (DICOM) format) that the image acquisition device 170 and the radiotherapy processing computing system 110 may use to perform operations consistent with the disclosed embodiments. Further, in some examples, the models discussed herein may be trained to process the original image data format or a derivation thereof.

In an example, the image acquisition device 170 may be integrated with the treatment device 180 as a single apparatus (e.g., an MRI device combined with a linear accelerator, also referred to as an "MRI-Linac"). Such an MRI-Linac can be used, for example, to determine a location of a target in the patient, so as to direct linear or circular radiation therapy accurately according to the radiation therapy treatment plan to a predetermined target. For instance, a radiation therapy treatment plan may provide information about a particular radiation dose to be applied to each patient. The radiation therapy treatment plan may also include other radiotherapy information and radiotherapy device parameters, such as beam angles, dose-histogram-volume information, the number of radiation beams to be used during therapy, the dose per beam, and the like.

The radiotherapy processing computing system 110 may communicate with an external database through a network to send/receive a plurality of various types of data related to image processing and radiotherapy operations. For example, an external database may include machine data (including device constraints) that provides information associated with the treatment device 180, the image acquisition device 170, or other machines relevant to radiotherapy or medical procedures. Machine data information may include radiation beam size, arc placement, beam on and off time duration, machine parameters, segments, MLC configuration, gantry speed, MRI pulse sequence, and the like. The external database may be a storage device and may be equipped with appropriate database administration software programs. Further, such databases or data sources may include a plurality of devices or systems located either in a central or a distributed manner.

The radiotherapy processing computing system 110 can collect and obtain data, and communicate with other systems, via a network using one or more communication interfaces, which are communicatively coupled to the processing circuitry 112 and the memory 114. For instance, a communication interface may provide communication connections between the radiotherapy processing computing system 110 and radiotherapy system components (e.g., permitting the exchange of data with external devices). For instance, the communication interface may, in some examples, have appropriate interfacing circuitry from an output device 146 or an input device 148 to connect to the user interface 142, which may be a hardware keyboard, a keypad, or a touch screen through which a user may input information into the radiotherapy system.

As an example, the output device 146 may include a display device that outputs a representation of the user interface 142 and one or more aspects, visualizations, or representations of the medical images, the treatment plans, and statuses of training, generation, verification, or implementation of such plans. The output device 146 may include one or more display screens that display medical images, interface information, treatment planning parameters (e.g., contours, dosages, beam angles, labels, maps, etc.), treatment plans, a target, localizing a target and/or tracking a target, or any related information to the user. The input device 148 connected to the user interface 142 may be a keyboard, a keypad, a touch screen or any type of device using which a user may input information to the radiotherapy system 100. Alternatively, the output device 146, the input device 148, and features of the user interface 142 may be integrated into a single device such as a smartphone or tablet computer (e.g., Apple iPad®, Lenovo Thinkpad®, Samsung Galaxy®, etc.).

Furthermore, any and all components of the radiotherapy system 100 may be implemented as a virtual machine (e.g., via VMWare, Hyper-V, and the like virtualization platforms) or independent devices. For instance, a virtual machine can be software that functions as hardware. Therefore, a virtual machine can include at least one or more virtual processors, one or more virtual memories, and one or more virtual communication interfaces that together function as hardware. For example, the radiotherapy processing computing system 110, the image data sources 150, or like components, may be implemented as a virtual machine or within a cloud-based virtualization environment.

The image acquisition device 170 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location, etc.). In an example, the image acquisition device 170 can acquire a 2D slice in any orientation. For example, an orientation of the 2D slice can include a sagittal orientation, a coronal orientation, or an axial orientation. The processing circuitry 112 can adjust one or more parameters, such as the thickness and/or orientation of the 2D slice, to include the target organ and/or target tumor. In an example, 2D slices can be determined from information such as a 3D CBCT or CT, or MRI volume. Such 2D slices can be acquired by the image acquisition device 170 in "near real-time" while a patient is undergoing radiation therapy treatment, for example, when using the treatment device 180 (with "near real-time" meaning acquiring the data without (or with minimal) lag between image acquisition and treatment, as known in the art).

Machine learning (ML) algorithms or techniques can be summarized as function approximation. Training data consisting of input-output pairs of some type (e.g., machine parameter(s) that are adjusted based on real-time patient anatomy information) are acquired from, e.g., expert clinicians, and a function is "trained" to approximate this mapping. Some methods involve neural networks. In these, a set of parametrized functions, $A_\theta$, are selected, where $\theta$ is a set of parameters (e.g., convolution kernels and biases) that are selected by minimizing the average error over the training data. If the input-output pairs are denoted by $(x_m, y_m)$, the function can be formalized by solving a minimization problem such as Equation 1:

$$\min_\theta \sum_{m=1}^{M} \|A_g(x_m) - y_m\|^2 \quad (1)$$

Once the network has been trained (e.g., $\theta$ has been selected), the function $A_\theta$ can be applied to any new input. For example, in the above setting of segmentation of CT images, a never-before-seen CT image can be fed into $A_\theta$, and a segmentation is estimated that matches what an expert clinician would find.

Simple neural networks consist of an input layer, a middle or hidden layer, and an output layer, each containing computational units or nodes. The hidden layer(s) nodes have input from all the input layer nodes and are connected to all nodes in the output layer. Such a network is termed "fully connected." Each node communicates a signal to the output node depending on a non-linear function of the sum of its inputs. For a classifier, the number of input layer nodes typically equals the number of features for each of a set of objects being sorted into classes and the number of output layer nodes is equal to the number of classes. A network is trained by presenting it with the features of objects of known classes and adjusting the node weights to reduce the training error by an algorithm called backpropagation. Thus, the trained network can classify novel objects whose class is unknown.

Neural networks have the capacity to discover relationships between the data and classes or regression values, and under certain conditions, can emulate any function including non-linear functions. In ML, an assumption is that the training and test data are both generated by the same data-generating process, $p_{data}$, in which each $\{x_i, y_i\}$ sample is identically and independently distributed (i.i.d.). In ML, the goals are to minimize the training error and to make the difference between the training and test errors as small as possible. Underfitting occurs if the training error is too large; overfitting occurs when the train-test error gap is too large. Both types of performance deficiency are related to model capacity; large capacity may fit the training data very well but lead to overfitting; small capacity may lead to underfitting.

Intra-fraction radiotherapy treatment workflow 130 communicates with the treatment data source 160 and/or the image data source 150 to determine a need to modify treatment device parameters in real time within a given fraction. In an embodiment, the intra-fraction radiotherapy treatment workflow 130 compares, at a particular time within the fraction, a current patient anatomy and/or a current amount of dose delivered to a target with an expected anatomy and/or dose specified in a treatment plan in accordance with a comparison function $f$. Based on a deviation between the current anatomy and/or amount and the expected anatomy and/or amount, the intra-fraction radiotherapy treatment workflow 130 modifies parameters of the radiotherapy device according to a function. The function may be any linear, quadratic function or other suitable mathematical expression that may indicate whether to increase, decrease, or make no adjustments to the radiotherapy device parameters based on the deviation. As an example, and without loss of generality, the comparison function $f$ may be represented by Equation 2:

$$f(t, I_{RT}(t), MU(t), I_{ref}(MU)) = \quad (2)$$
$$\begin{cases} > 0 & I_{RT}(t) \text{ more favorable than } I_{ref}(MU) \\ = 0 & I_{RT}(t) \text{ as favorable as } I_{ref}(MU) \\ < 0 & I_{RT}(t) \text{ less favorable than } I_{ref}(MU) \end{cases}$$

where t represents the current time in a given treatment fraction, $I_{RT}(t)$ represents the patient anatomy at the current time in the given treatment fraction, $MU(t)$ represents the monitor units (MU) delivered at the current time in the given treatment fraction, and $I_{ref}(MU)$ represents the patient anatomy for the reference treatment plan for after MU monitor units of the given treatment fraction.

The machine settings at time t during a radiotherapy treatment (intra-fraction) can be defined by the vector $\tau$. The adaptation strategy translates the value of the comparison function $f$ to updated machine settings $\tau'$ based on a parameter vector $\mu$. In an implementation, the machine settings can be represented by Equation 3:

$$\tau' = \tau'(\tau, f, \mu, t) \quad (3)$$

The adaptation strategy is described by $\tau'$ in terms of the degree and type of adaptation. For example, the type of adaptation can specify what radiotherapy machine parameters are to be adjusted (e.g., the dose amount per time, the collimator settings (e.g., jaw and MLC leaf positions), the gantry rotation speed, and/or any combination thereof) and the degree specifies the amount by which the parameters are adjusted. In some cases, the MLC jaw and leaf positions might be treated as independent parameters, such that one leaf and/or jaw position is adjusted by a first amount and a second leaf is adjusted by a second amount. The parameters $\mu$ are subject to tuning by simulation, optimization, machine learning or heuristics. The vector $\tau'$ may describe all machine settings but may be simplified to only contain those machine settings that are subject to adaptation for the chosen scheme. The mathematical expression of the components of the vector $\tau'$ may be any linear or non-linear mathematical expression and the components of the vector $\tau'$ may be determined by solving a linear or non-linear optimization problem. In certain implementations, the function $\tau'(\tau, f, \mu, t)$ of Equation 3 can take the form of a non-linear system or other suitable mathematical expression.

The parameters $\mu$ are subject to tuning by simulation, optimization, machine learning or heuristics as part of the treatment planning process to determine the adaptation scheme. The parameters $\mu$ can also be determined at the time of adaptation my means of simulation, optimization, machine learning or heuristics.

In one embodiment, the function $\tau'$ ($\tau, f, \|, t$) of Equation 3 may be a linear system where the i=1, ..., N and the updated machine settings $\tau'_i$ is determined by linear functions $\gamma_{1,i}$ and $\gamma_{2,i}$ in accordance with Equation 4:

$$\tau'_i(f, \gamma_{1,i}, \gamma_{2,i}, \alpha_{1,i}, \alpha_{2,i}) = \begin{cases} \tau_i \cdot \gamma_{1,i}(f) & f < \alpha_{1,i} \\ \tau_i & f \geq \alpha_{1i} \text{ and } f \leq \alpha_{2,i} \\ \tau_i \cdot \gamma_{2,i}(f) & f > \alpha_{2,i} \end{cases} \quad (4)$$

According to Equation 4, when $\eta \in [\alpha_{1,i}, \alpha_{2,i}]$ such an interval is one where no adaptation is made for the ith machine setting and when $f \notin [\alpha_{1,i}, \alpha_{2,i}]$ the adaptation is governed by $\gamma_{1,i}$ and $\gamma_{2,i}$ for the same machine setting. Here, $\mu$ consists of all the parameters in functions $\gamma_{1,i}$, $\gamma_{2,i}$ and constants $\alpha_{1,i}$ and $\alpha_{2,i}$ for all i=1 ... N. The value of may differ for different i.

For example, the collimator settings of the radiotherapy device (e.g., the positions of the jaws and the leaves of the MLC and amount by which the positions of the leaves are changed) that are part of $\tau$ and their adaptation $\tau'$ may be associated with the output of the function $f$. Namely, the comparison function $f$ may provide a result that indicates based on an output of Equations 3 or 4 the adjustment, if any, needed to the jaws and MLC leaf positions to change a shape of the collimator opening. As such, the collimator settings described by components in $\tau$ are adapted according to Equation 3. As another example, the gantry rotation speed (described by components in $\tau$) may be similarly associated with the function $f$. As such, the adapted gantry rotation speed, part of $\tau'$, is adapted according to Equation 3. As another example, the dose amount per time (dose per unit time) (also part of $\tau$) may be similarly associated by the function $f$. As such, the updated dose amount per time (part of $\tau'$) is determined using Equation 3.

The intra-fraction radiotherapy treatment workflow 130 may be configured to track the amount of adjustment of the parameters of the radiotherapy device throughout a given treatment fraction. Specifically, the intra-fraction radiotherapy treatment workflow 130 may detect that the function of Equation 3 specifies a given adjustment (e.g., increasing the dose amount) to the parameters of the radiotherapy device. In response, prior to making the adjustment to the treatment data source 160, the intra-fraction radiotherapy treatment workflow 130 may determine whether the total amount of dose delivered to the target until the current time in the treatment fraction exceeds the prescribed dose amount in the treatment plan. If the total amount of dose delivered until the current time does not exceed the prescribed dose amount, the intra-fraction radiotherapy treatment workflow 130 may determine whether making the adjustment, specified by Equation 3, will result in the total amount of dose delivered to the target, after making the adjustment in the given treatment fraction, exceed the prescribed dose amount. If the prescribed dose amount will be exceeded, the intra-fraction radiotherapy treatment workflow 130 may pause, terminate, reduce, or not perform the modification specified in Equation 3. If the prescribed dose amount will not be exceeded, the intra-fraction radiotherapy treatment workflow 130 may communicate the adjustment specified in Equation 3 to the treatment data source 160 to increase (or change) the dose amount.

In some embodiments, the intra-fraction radiotherapy treatment workflow 130 may determine that at a particular time within the given treatment fraction, Equation 3 specifies parameters that will cause an increase in the amount of delivered dose within the given treatment fraction relative to what is prescribed in the treatment plan. As a result, the intra-fraction radiotherapy treatment workflow 130 may cause the treatment device 180 to deliver the increased amount of dose at the particular time. After the particular time and for subsequent times in the given treatment fraction, the intra-fraction radiotherapy treatment workflow 130 may retrieve the dose amounts prescribed in the treatment plan for the subsequent times. The intra-fraction radiotherapy treatment workflow 130 may reduce each of the dose amounts for the subsequent times by equal or non-equal amounts such that a total dose amount delivered to the target at the subsequent times in the given fraction is equal to the amount by which the dose at the particular time was increased. This ensures that even though the dose may be increased as a consequence of applying Equation 3 at a particular time in a given treatment fraction, the total amount of dose delivered to the target within the treatment fraction remains the same as that which is prescribed in the treatment plan.

In some embodiments, the intra-fraction radiotherapy treatment workflow 130 may determine that at a particular time within the given treatment fraction, Equation 3 specifies parameters that will cause a decrease in the amount of delivered dose within the given treatment fraction relative to what is prescribed in the treatment plan. As a result, the intra-fraction radiotherapy treatment workflow 130 may cause the treatment device 180 to deliver the decreased amount of dose at the particular time. After the particular time and for subsequent times in the given treatment fraction, the intra-fraction radiotherapy treatment workflow 130 may retrieve the dose amounts prescribed in the treatment plan for the subsequent times. The intra-fraction radiotherapy treatment workflow 130 may increase each of the dose amounts for the subsequent times by equal or non-equal amounts such that a total dose amount delivered to the target at the subsequent times in the given fraction is equal to the amount by which the dose at the particular time was decreased. This ensures that even though the dose may be decreased according to Equation 3 at a particular time in a given treatment fraction, the total amount of dose delivered to the target within the treatment fraction remains the same as that which is prescribed in the treatment plan.

In some embodiments, the intra-fraction radiotherapy treatment workflow 130 may compute the $I_{RT}(t)$ that represents the patient anatomy at the current time in the given treatment fraction using real-time patient anatomy processing 132. Radiotherapy treatment, radiation therapy, and radiotherapy are used interchangeable throughout this disclosure and should be understood to have the same meaning. Real-time patient anatomy processing 132 may communicate with image acquisition device 170 and/or treatment device 180 to receive one or more images of the patient in real-time within a given treatment fraction and/or the dosimetric quantity observed during radiation. The real-time patient anatomy processing 132 may utilize a predetermined patient motion model to compute the current patient anatomy from the images received from the image acquisition device 170. The real-time patient anatomy processing 132 may determine a result of Equation 2 (e.g., the amount of target (e.g., tumor) overlap with the OAR at a given time in a treatment fraction, a distance between a border of the target and the OAR (e.g., the separation between prostate and rectum), dosimetric quantity observed during radiation delivery, a dose to the target as a function of depth, and/or an uncertainty associated with the computed patient anatomy). Overlap between an OAR and target refers to the amount of overlap from a radiation beam's eye view—namely how much percentage or quantity of the radiation beam will be delivered to the target versus the OAR. The greater the overlap, the greater the amount of radiation that will be delivered to the OAR and the lower the overlap, the lower amount of radiation that will be delivered to the OAR.

In some embodiments, the intra-fraction radiotherapy treatment workflow 130 may retrieve, from memory, the $I_{ref}(MU(t))$ that represents the reference patient anatomy specified in a treatment plan for the current time in the given treatment fraction using reference patient anatomy processing 134. The reference patient anatomy processing 134 may provide the amount of target (e.g., tumor) overlap with the OAR expected at a given time in a treatment fraction, an expected distance between a border of the target and the OAR (e.g., the separation between prostate and rectum), an expected dosimetric quantity observed during radiation delivery, an expected dose to the target as a function of depth, and/or an expected uncertainty associated with the computed patient anatomy.

In some embodiments, the intra-fraction radiotherapy treatment workflow 130 may compute an output of function $f$ of Equation 2 and the adjustment (if any) specified by Equation 3 using radiotherapy device parameter adaptation workflow 140. Specifically, radiotherapy device parameter adaptation workflow 140 may compare the output of the real-time patient anatomy processing 132 with the output of the reference patient anatomy processing 134. In an example, the radiotherapy device parameter adaptation workflow 140 may compare the amount of target (e.g., tumor) overlap with the OAR at a given time in a treatment fraction with the expected amount for the current time. The radiotherapy device parameter adaptation workflow 140 may determine whether the comparison indicates that the current patient anatomy provided by the real-time patient anatomy processing 132 is more favorable than the patient anatomy provided by reference patient anatomy processing 134. Specifically, the radiotherapy device parameter adaptation workflow 140 may, according to Equation 2, determine that the amount of target (e.g., tumor) overlap with the OAR at a given time is less than the expected overlap by an amount specified by one or more of the parameters $\mu$ of Equation 3 and is thereby more favorable. In such circumstances, the output of the function $f$ of Equation 2 may be a value greater than 0. The radiotherapy device parameter adaptation workflow 140 may determine that the amount of target (e.g., tumor) overlap with the OAR at a given time is more than the expected overlap and is thereby less favorable. In such circumstances, the output of the function $f$ of Equation 2 may be a value less than 0.

The adaptation selection workflow 136 may select the parameter, specified by Equation 3, of the treatment device 180 to which the function $f$ corresponds. The parameter of the treatment device 180 may be based on the type of patient anatomy that is obtained and compared by the radiotherapy device parameter adaptation workflow 140. For example, the adaptation selection workflow 136 may select a dose amount as the parameter when the type of patient anatomy that is compared is an amount of target (e.g., tumor) overlap with the OAR. In such cases, the output of the function $f$ may correspond to a dose amount that is delivered by the treatment device 180. In such cases, the radiotherapy device parameter adaptation workflow 140 may obtain one or more of the parameters $\mu$ of Equation 3 to determine the amount by which to increase or decrease the dose at a subsequent time in the same treatment fraction.

As another example, the adaptation selection workflow 136 may select the dose as function of depth along a beam axis when the type of patient anatomy that is compared is a relative 3D position of the target and the OAR (e.g., whether the OAR has moved more proximal or distal to the target in the beam direction). Namely, the adaptation selection workflow 136 may consider how the dose changes as a function of depth due to the interaction of the radiation with the tissue. For example, if the separation on depth between the target and the OAR has changed, then the relative dose to them has changed. In such cases, the real-time patient anatomy processing may utilize raytracing from the source of radiation until the target and/or OAR is hit or distance transform measuring the Euclidean distance from the target surface. In some other cases, the relative depth of the target and the OAR(s) can be determined in order to calculate the change in the dose. Specifically, either the distance from all points of the OAR is projected onto the isocenter plan or only the distance of some point of interest. The output of the function $f$ may correspond to changes in dose that is delivered by the treatment device 180 as a function of depth. In such cases, the radiotherapy device parameter adaptation workflow 140 may obtain one or more parameters from $\mu$ of Equation 3 to determine the amount by which to increase or decrease the dose as a function of depth at a subsequent time in the same treatment fraction.

As another example, the adaptation selection workflow 136 may select whether to pause irradiation or switch to another segment (e.g., part of the treatment within a given fraction) in the treatment plan as the parameter when the type of patient anatomy that is compared is a current dosimetry (provided by the real-time patient anatomy processing 132) relative to the expected dosimetry (provided by the reference patient anatomy processing 134). In such cases, the output of the function $\tau'$ may correspond to a decision of whether to pause radiation and/or to which segment or time in the fraction to skip to. In cases where radiation is paused, the output of Equation 3 may specify that the paused radiation be resumed at a later time or segment in the fraction (e.g., when the situation is more favorable relative to what is expected in the treatment plan or at the end of the fraction). According to this example, the sequence of irradiations specified in the treatment plan for a given fraction can be reordered with respect to the current patient geometry to deliver the treatment plan in the most favorable and optimal way that maximizes exposure of radiation to the target and minimizes exposure to the OAR. In some implementations, instead of, or in addition to, reordering the sequence of irradiations, adaptation selection workflow 136 may select to divide the irradiations prescribed in the treatment plan over n times, where each time the MU of the partial segment is set to $MU_{segment}/n$. $MU_{segment}$ specifies the amount of MU in a given segment within a fraction. Namely, the amount of radiation in each segment specified in the treatment plan is reduced by an amount corresponding to the number of times n over which the segments are repeated. This way, the amount of radiation delivered to the target specified by the treatment plan is maintained. Specifically, the treatment plan may specify an amount of radiation MU to deliver at a particular segment, and this amount is divided by the total number of repetitions n. Because the same segment will receive the divided amount of radiation n times, the segment will receive the specified amount of radiation MU at the end of the fraction. In addition, the adaptation selection workflow 136 may add one or more segments to a radiotherapy treatment plan to perform re-scanning and increase times when one or more regions of the patient anatomy are irradiated within the given radiotherapy treatment fraction or to irradiate regions of the patient anatomy that are additional and different from regions specified to be irradiated in the radiotherapy treatment plan.

As another example, the adaptation selection workflow 136 may select the dose to deliver in a next adjacent or non-adjacent time in the fraction, as function of an estimate of the amount of dose that remains to be delivered within the given fraction to the particular region that has already been irradiated or another region. Namely, the adaptation selection workflow 136 may consider how much total dose remains to be delivered in the treatment plan for the given fraction and compare that dose to how much dose has already been delivered within the given fraction. The adaptation selection workflow 136 may increase the dose that is delivered in the next adjacent or non-adjacent time in the fraction in response to determining that the estimated remaining dose that remains to be delivered to the region is less than a threshold or may decrease the dose that is delivered in the next adjacent or non-adjacent time in the fraction in response to determining that the estimated remaining dose that remains to be delivered to the region is more than the threshold. The adaptation selection workflow 136 may also consider whether the next adjacent or non-adjacent time in the fraction is closer to the start of the fraction or closer to an end of the fraction (e.g., is within a specified number of irradiation intervals of the start/end of the fraction) in making the adjustment. For example, the radiotherapy treatment dose may be delivered to a given region in the patient anatomy at a first time and the adaptation selection workflow 136 determines whether the given region in the patient anatomy will be irradiated by the radiotherapy device at another time within the given radiotherapy treatment fraction. The adaptation selection workflow 136 modifies the amount of radiotherapy treatment dose delivered at the second time as a function of the determination of whether the given region in the patient anatomy will be irradiated by the radiotherapy device at another time within the given radiotherapy treatment fraction.

In some embodiments, in response to determining that the dose at a subsequent time (e.g., at a subsequent segment) is to be reduced (e.g., because the overlap between the target and the OAR is greater than expected), the radiotherapy device parameter adaptation workflow 140 may determine whether a remaining set of segments in the treatment fraction, following the subsequent time, in the treatment plan will deliver dose to the target. If not, the dose may be prevented from being reduced even though there is a high risk of exposing the OAR to the radiation. In this way, if a part of a tumor that is treated with the current segment of the treatment plan will not receive the dose from any subsequent delivery, that part of the tumor will not be blocked from receiving radiation (or the dose amount per time will not be reduced by as much as specified by Equation 3) even if the OAR is irradiated. Estimates of the dose from subsequent delivery in the treatment fraction can be determined by analyzing whether the beam shape output by the treatment device 180 overlaps the considered part of the tumor.

As another example, the adaptation selection workflow 136 may select an MLC setting as the adaptation parameter when the type of patient anatomy that is compared is an amount of target (e.g., tumor) overlap with the OAR. In such cases, one of the outputs of the function $\tau'$ of Equation 3 may correspond to a collimator setting adjustment (e.g., a shape of the collimator opening defined by positions of the jaws and the leaves of the MLC) of the treatment device 180. In such cases, the radiotherapy device parameter adaptation workflow 140 may obtain the parameter from one or more parameter of $\mu$ of Equation 3 to determine the amount by which to move or change positions of individual ones or collections of leaves of the MLC setting at a subsequent time in the same treatment fraction.

As another example, the adaptation selection workflow 136 may select the dose amount per time (or any other radiotherapy parameter of Equation 3) as the adaptation parameter when the type of patient anatomy that is compared is an uncertainty of the patient anatomy provided by the real-time patient anatomy processing 132. Specifically, the real-time patient anatomy processing 132 may determine the current patient anatomy from 2D MR, 2D X-ray or X-ray projections, markers visible on X-ray or transponders, each of which is associated with some level of uncertainty. In such cases, the output of the function $\tau'$ of Equation 3 may correspond to a dose amount per time of the treatment device 180 based on the current level of uncertainty relative to the expected level of uncertainty specified by the reference patient anatomy processing 134. In such cases, the radiotherapy device parameter adaptation workflow 140 may obtain one or more parameter from $\mu$ of Equation 3 to determine the amount by which to increase or decrease the dose amount per time at a subsequent time in the same treatment fraction. According to this example, if the target structure is uncertain, the adaptation computed by Equation 3 can be made more restrictive to reduce the adjustment of the parameters or avoid adjustment altogether to not cause underdosage. A more conservative adaptation strategy for Equation 3 can be applied if the uncertainty is high.

The adaptation selection workflow 136 may utilize ML techniques to compute various parameters of the functions of Equations 2 and/or 3. Such techniques are described in connection with FIG. 3 below. Specifically, adaptation selection workflow 136 may utilize some heuristics, exhaustive search through multiple treatment simulations or solve an optimization problem to determine the parameters of Equations 2 and 3, and specifically the parameters $\mu$. The optimization problem can be set up to balance the trade-off of radiotherapy (e.g., dose to the target versus dose to the OARs).

Figure 2:
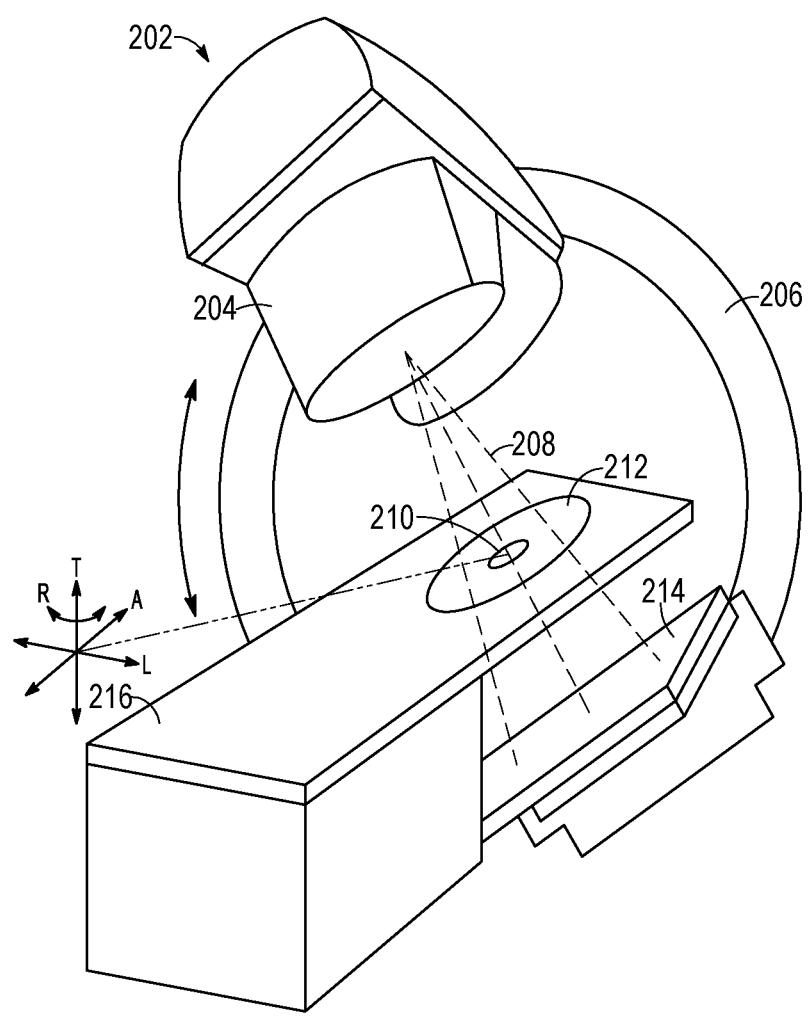
FIG. 2 illustrates an exemplary image-guided radiotherapy device according to some examples of the disclosure.

FIG. 2 illustrates an exemplary image-guided radiation therapy device 202 that includes a radiation source, such as an X-ray source or a linear accelerator, a couch 216, an imaging detector 214, and a radiation therapy output 204. The radiation therapy device 202 may be configured to emit a radiation therapy beam 208 to provide therapy to a patient. The radiation therapy output 204 can include one or more attenuators or collimators, such as a multi-leaf collimator (MLC).

As an example, a patient can be positioned in a region 212, supported by the treatment couch 216, to receive a radiation therapy dose according to a radiation therapy treatment plan. The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an example, gantry 206 may be continuously rotatable around couch 216 when the couch 216 is inserted into the treatment area. In another example, gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation therapy beam 208 according to a radiation therapy treatment plan. Both the couch 216 and the gantry 206 are independently moveable from one another in multiple degrees of freedom, which allows the patient to be positioned such that the radiation therapy beam 208 can precisely target the tumor.

The coordinate system (including axes A, T, and L) can have an origin located at an isocenter 210. The isocenter 210 can be defined as a location where the central axis of the radiation therapy beam 208 intersects the origin of a coordinate axis, such as to deliver a prescribed radiation dose to a location on or within a patient. Alternatively, the isocenter 210 can be defined as a location where the central axis of the radiation therapy beam 208 intersects the patient for various rotational positions of the radiation therapy output 204 as positioned by the gantry 206 around the axis A.

Gantry 206 may also have an attached imaging detector 214. The imaging detector 214 is preferably located opposite to the radiation source (output 204), and in an example, the imaging detector 214 can be located within a field of the radiation therapy beam 208. The imaging detector 214 can be mounted on the gantry 206, preferably opposite the radiation therapy output 204, such as to maintain alignment with the radiation therapy beam 208. The imaging detector 214 rotates about the rotational axis as the gantry 206 rotates. In an example, the imaging detector 214 can be a flat panel detector (e.g., a direct detector or a scintillator detector). In this manner, the imaging detector 214 can be used to monitor the therapy beam 208, or the imaging detector 214 can be used for imaging the patient's anatomy, such as portal imaging. The control circuitry of the radiation therapy device 202 may be integrated within the radiotherapy system 100 or remote from it.

In an illustrative example, one or more of the couch 216, the therapy output 204, or the gantry 206 can be automatically positioned, and the therapy output 204 can establish the radiation therapy beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue nearby the therapy locus can be reduced or avoided.

Thus, FIG. 2 specifically illustrates an example of a radiation therapy device 202 operable to provide radiotherapy treatment to a patient consistent with or according to a radiotherapy treatment plan and parameters of a device adjusted within a given fraction, with a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient. In another example, a radiation therapy device can be a combination of a linear accelerator and an image acquisition device. In some examples, the image acquisition device may be an MRI, an X-ray, a CT, a CBCT, a spiral CT, a PET, a SPECT, an optical tomography, a fluorescence imaging, ultrasound imaging, or radiotherapy portal imaging device, etc., as would be recognized by one of ordinary skill in the art.

Figure 3:
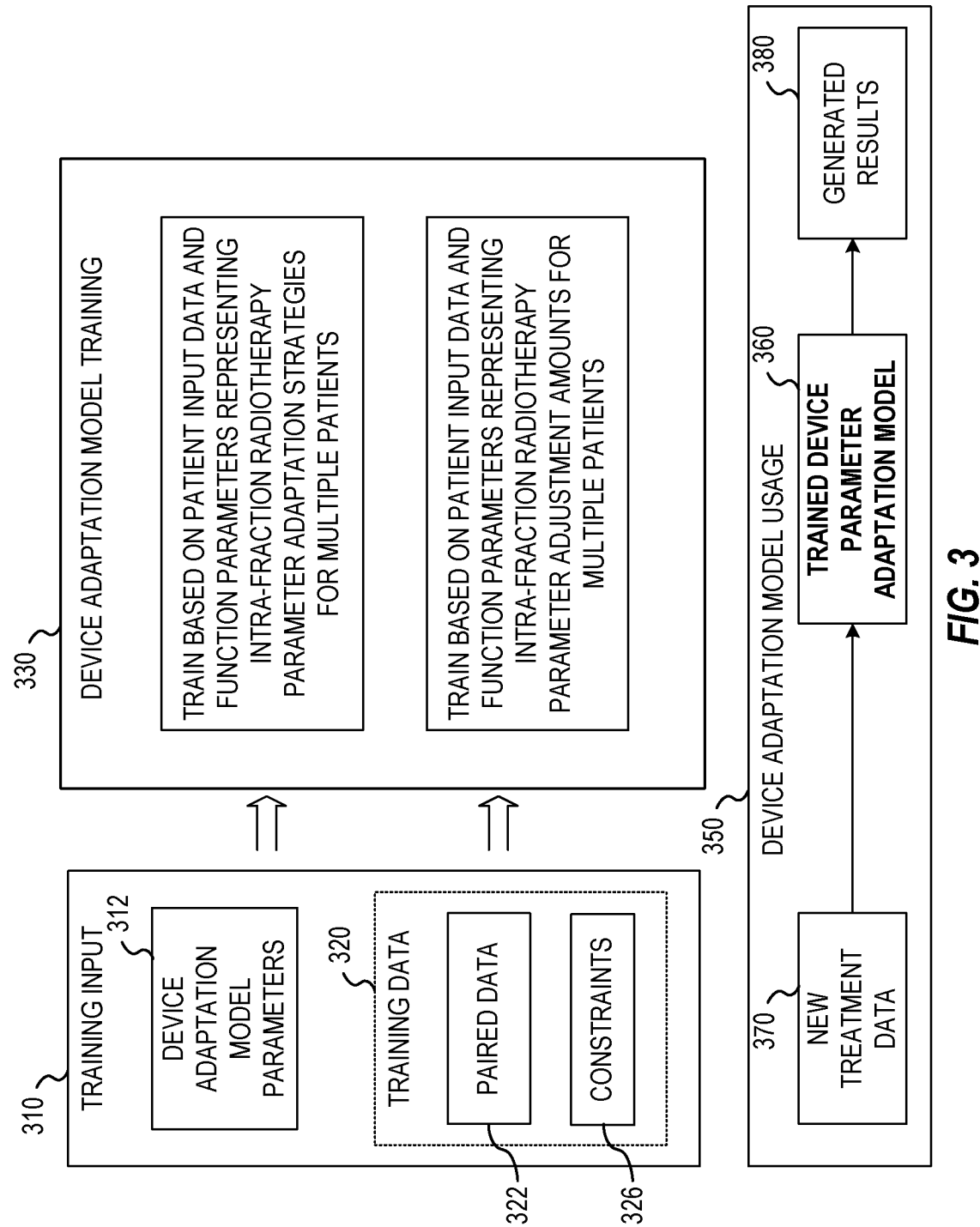
FIG. 3 illustrates an exemplary data flow for training and use of a machine learning technique to generate a device adaptation model according to some examples of the disclosure.

FIG. 3 illustrates an exemplary data flow for training and use of a machine learning technique to generate a device adaptation model and/or determination of radiotherapy device parameters according to some examples of the disclosure including the computation of such parameters according to an optimization problem. The data flow includes training input 310, device adaptation model training 330, and device adaptation model usage 350. The trained device parameter adaptation model 360 provides one or more parameters of the functions of Equations 2 and 3. For example, the trained device parameter adaptation model 360 provides the parameters $\mu$ and may provide the radiotherapy device parameter that is output for adjustment ($\tau'$).

Training input 310 includes device adaptation model parameters 312 and training data 320, which may include paired training data sets 322 (e.g., input-output training pairs) and constraints 326. Device adaptation model parameters 312 stores or provides the parameters or coefficients of the machine learning technique $A_\theta$ used to compute and provide the parameters $\mu$ for a given patient. During training, these parameters 312 are adapted or computed according to an optimization problem based on the input-output training pairs of the training data sets 322. After the parameters 312 are adapted (after training), the parameters 312 are used by the trained device parameter adaptation model 360 to implement the trained machine learning technique $A_\theta$ on a new set of treatment data 370 (e.g., a new set of patient information for a new patient). The paired data sets 322 may specify relationship pairs of the treatment information of each patient and the corresponding intra-fraction radiotherapy parameter adaptation strategy and/or parameter adjustment amount utilized to treat the given patient. For example, the paired data sets 322 may specify the amount of dose that is increased or decreased (e.g., the parameter adjustment amount) at a given time in a treatment fraction for a particular patient when the target-to-OAR overlap was within a certain amount (e.g., the adaptation strategy).

Training data 320 includes constraints 326, which may define the physical constraints of a given radiotherapy device. These constraints 326 are used to adapt an estimated intra-fraction radiotherapy model parameter to actual corresponding parameters used in a given simulation or for a given patient or set of patients according to an optimization problem. The paired data sets 322 may include a first set of input-output pairs, such as a given set of prior patient input parameters (e.g., MR images) and the corresponding intra-fraction radiotherapy parameter adaptation strategy $\mu$ defining the intra-fraction radiotherapy parameter type and adjustment amount.

Device adaptation model training 330 trains the machine learning technique $A_\theta$ based on the input-output pairs of paired data sets 322 and according to an optimization problem. For example, the device adaptation model training 330 may train the device adaptation model parameters 312 by minimizing a first loss function based on a training patient input data and the function of Equation 2 or 3 parameters that represent the intra-fraction radiotherapy parameter adaptation strategies for multiple patients. For example, the parameter adaptation strategy may correspond to modifying dose based on target-to-OAR overlap. In such cases, the parameter adaptation strategy may estimate the parameters of $\mu$ to control whether to increase or decrease the corresponding dose in a subsequent time or segment of the given fraction. The device adaptation model training 330 may train the device adaptation model parameters 312 by minimizing a second loss function based on a training patient input data and the function of Equation 2 or 3 parameters that represent the intra-fraction radiotherapy parameter adjustment amounts for multiple patients. For example, the parameter adaptation strategy may correspond to modifying dose based on a distance between a border of a tumor and an OAR. In such cases, the parameter adaptation strategy may estimate a value for the parameters of $\mu$ to control the amount by which to increase or decrease the corresponding dose in a subsequent time or segment of the given fraction. The result of minimizing these loss functions for multiple sets of training data trains, adapts, or optimizes the device adaptation model parameters 312. In this way, the machine learning technique is trained to establish a relationship between the particular type of input parameter and intra-fraction function parameters.

In some embodiments, the device adaptation model training 330 trains the machine learning technique by retrieving training imaging information for a training patient in which the training imaging information represents a plurality of patient anatomies during the training radiotherapy treatment fraction. A reference training patient anatomy for the training radiotherapy treatment fraction is retrieved. Each of the plurality of patient anatomies represented by the training imaging information is paired with the reference training patient anatomy. The device adaptation model training 330 establishes, for the training radiotherapy treatment fraction, ground truth intra-fraction radiotherapy treatment parameters for the training radiotherapy treatment fraction for the function by simulating dose delivered to the training patient throughout the training radiotherapy treatment fraction. The device adaptation model training 330 determines a deviation between a given one of the plurality of patient anatomies and the reference training patient anatomy at a given point in the training radiotherapy treatment fraction. The device adaptation model training 330 identifies a given set of the one or more intra-fraction radiotherapy treatment parameters used in the training radiotherapy treatment fraction in presence of the determined deviation at the given point. The device adaptation model training 330 trains the machine learning technique based on a deviation between the identified given set of the one or more intra-fraction radiotherapy treatment parameters and the ground truth intra-fraction radiotherapy treatment parameters.

After the machine learning technique $A_\theta$ is trained, new treatment data 370 including one or more patient input parameters (e.g., an MR image, a medical image, segmentation information of an object of interest associated with the patient, diagnosis, or dose prescription information) may be received. The trained machine learning technique $A_\theta$ may be applied to the new treatment data 370 to generate generated results 380 including one or more parameters of the intra-fraction radiotherapy function parameters (e.g., of Equations 2 and 3). In this way, after many patients with the same diagnosis, prescription, treatment planning strategy, and choice of parameters for Equations 2 and 3 have been treated, the resulting distribution of Equation 3 can be analyzed and used to treat a new patient with similar conditions or circumstances. In an embodiment, the device adaptation model can be trained to find a class solution (e.g., using an ML technique or other suitable processes) that will fit most patients of the same group, which makes it possible to avoid tuning the parameters to the individual patient. The parameters for Equations 2 and 3 can also be determined by comparing the current patient information with previously treated patients and extracting the corresponding parameters of Equations 2 and 3 used to treat those patients.

Figure 4:
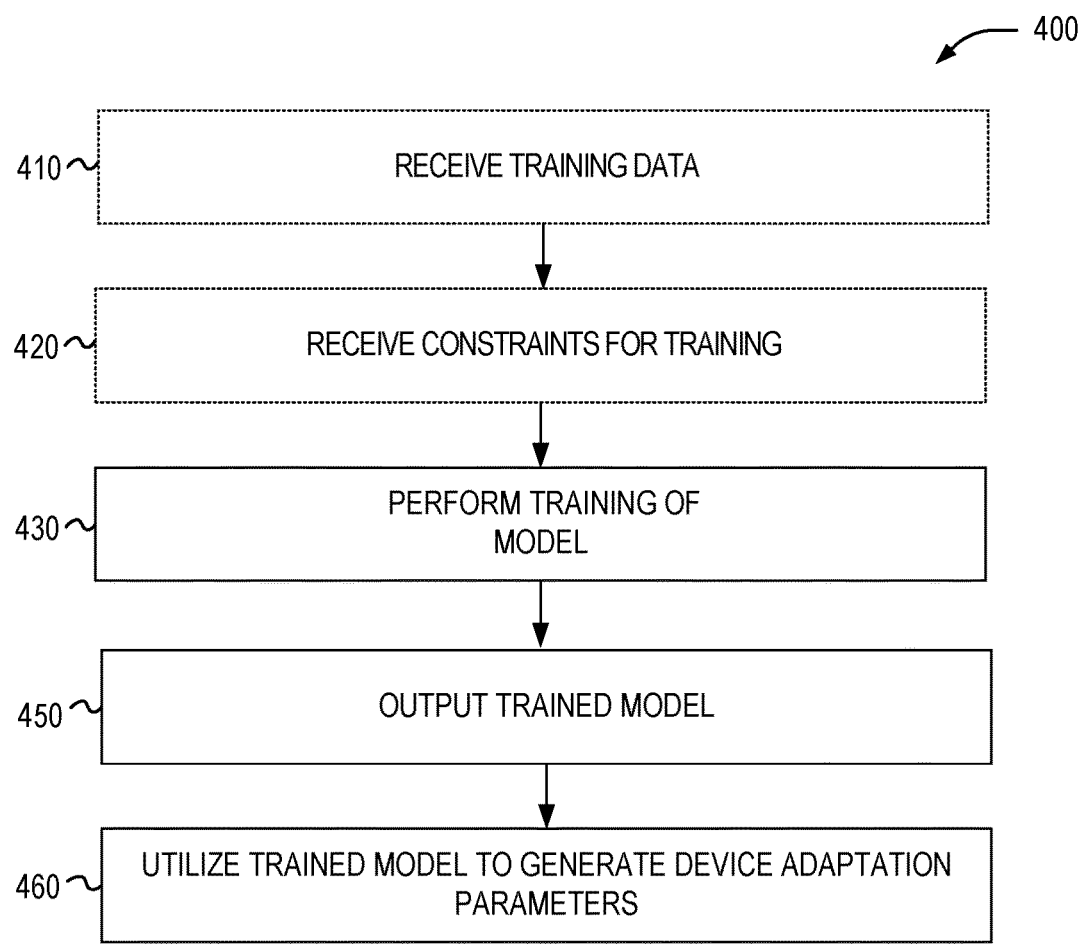
FIGS. 4-6 illustrate flowcharts of exemplary operations for training and using a machine learning technique to perform intra-fraction radiotherapy treatment according to some examples of the disclosure.

FIG. 4 is a flowchart illustrating example operations of the treatment processing logic 120 in performing process 400, according to example embodiments. The process 400 may be embodied in computer-readable instructions for execution by one or more processors such that the operations of the process 400 may be performed in part or in whole by the functional components of the treatment processing logic 120; accordingly, the process 400 is described below by way of example with reference thereto. However, in other embodiments, at least some of the operations of the process 400 may be deployed on various other hardware configurations. The process 400 is therefore not intended to be limited to the treatment processing logic 120 and can be implemented in whole, or in part, by any other component. Some or all of the operations of process 400 can be in parallel, out of order, or entirely omitted.

At operation 410, treatment processing logic 120 receives training data. For example, treatment processing logic 120 receives training data 320, which may include paired training data sets 322 (e.g., input-output training pairs).

At operation 420, treatment processing logic 120 receives constraints for training the model. For example, treatment processing logic 120 receives constraints 326.

At operation 430, treatment processing logic 120 performs training of the model in accordance with device adaptation model training 330.

At operation 450, treatment processing logic 120 outputs the trained model. For example, treatment processing logic 120 outputs the trained device parameter adaptation model 360 to operate on a new set of treatment data 370 to perform intra-fraction radiotherapy device parameter adjustments.

At operation 460, treatment processing logic 120 utilizes the trained model to generate device adaptation parameters.

Figure 5:
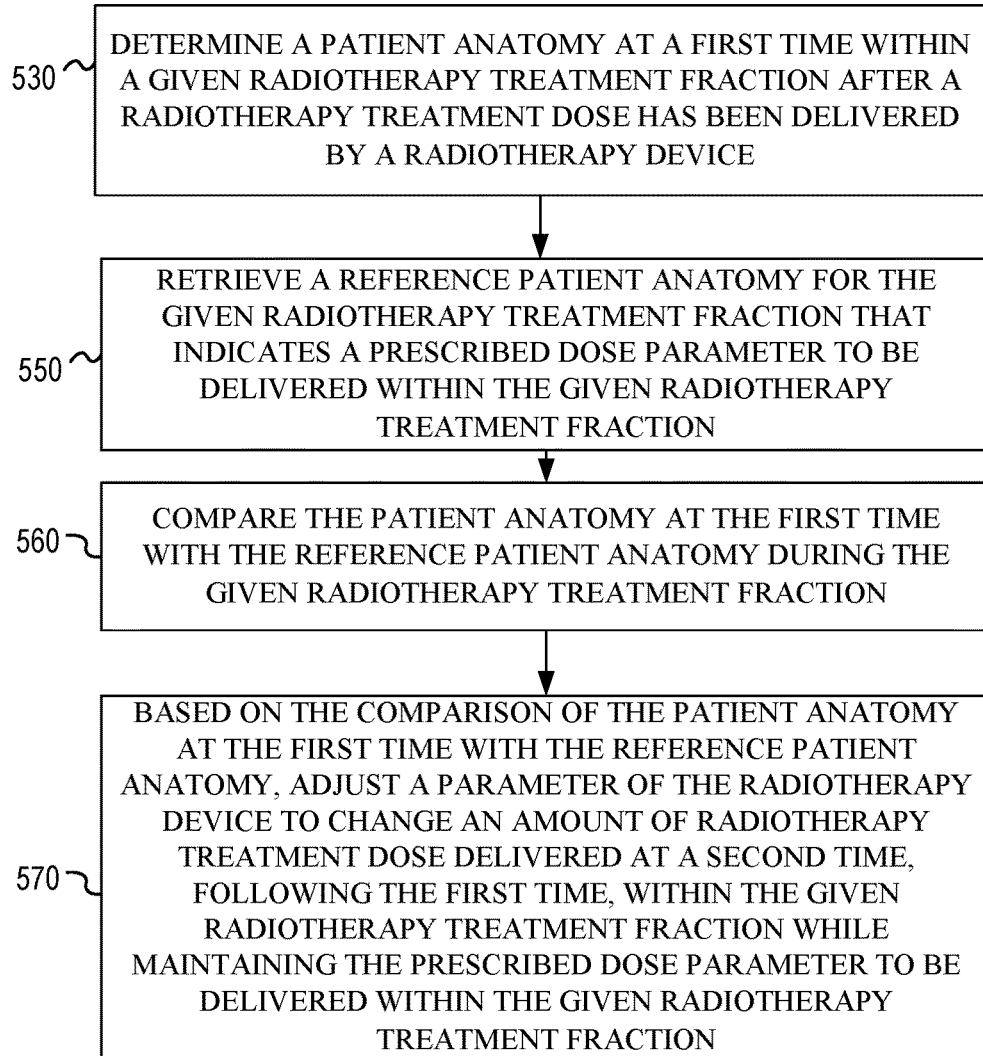

FIG. 5 is a flowchart illustrating example operations of the treatment processing logic 120 in performing process 500, according to example embodiments. The process 500 may be embodied in computer-readable instructions for execution by one or more processors such that the operations of the process 500 may be performed in part or in whole by the functional components of the treatment processing logic 120; accordingly, the process 500 is described below by way of example with reference thereto. However, in other embodiments, at least some of the operations of the process 500 may be deployed on various other hardware configurations. The process 500 is therefore not intended to be limited to the treatment processing logic 120 and can be implemented in whole, or in part, by any other component. Some or all of the operations of process 500 can be in parallel, out of order, or entirely omitted.

At operation 530, treatment processing logic 120 determines a patient anatomy at a first time within a given radiotherapy treatment fraction after a radiotherapy treatment dose has been delivered by a radiotherapy device.

At operation 550, treatment processing logic 120 retrieves a reference patient anatomy for the given radiotherapy treatment fraction that indicates a prescribed dose parameter to be delivered within the given radiotherapy treatment fraction.

At operation 560, treatment processing logic 120 compares the patient anatomy at the first time with the reference patient anatomy during the given radiotherapy treatment fraction.

At operation 570, treatment processing logic 120, based on the comparison of the patient anatomy at the first time with the reference patient anatomy, adjusts a parameter of the radiotherapy device to change an amount of radiotherapy treatment dose delivered at a second time, following the first time, within the given radiotherapy treatment fraction while maintaining the prescribed dose parameter to be delivered within the given radiotherapy treatment fraction.

Figure 6:
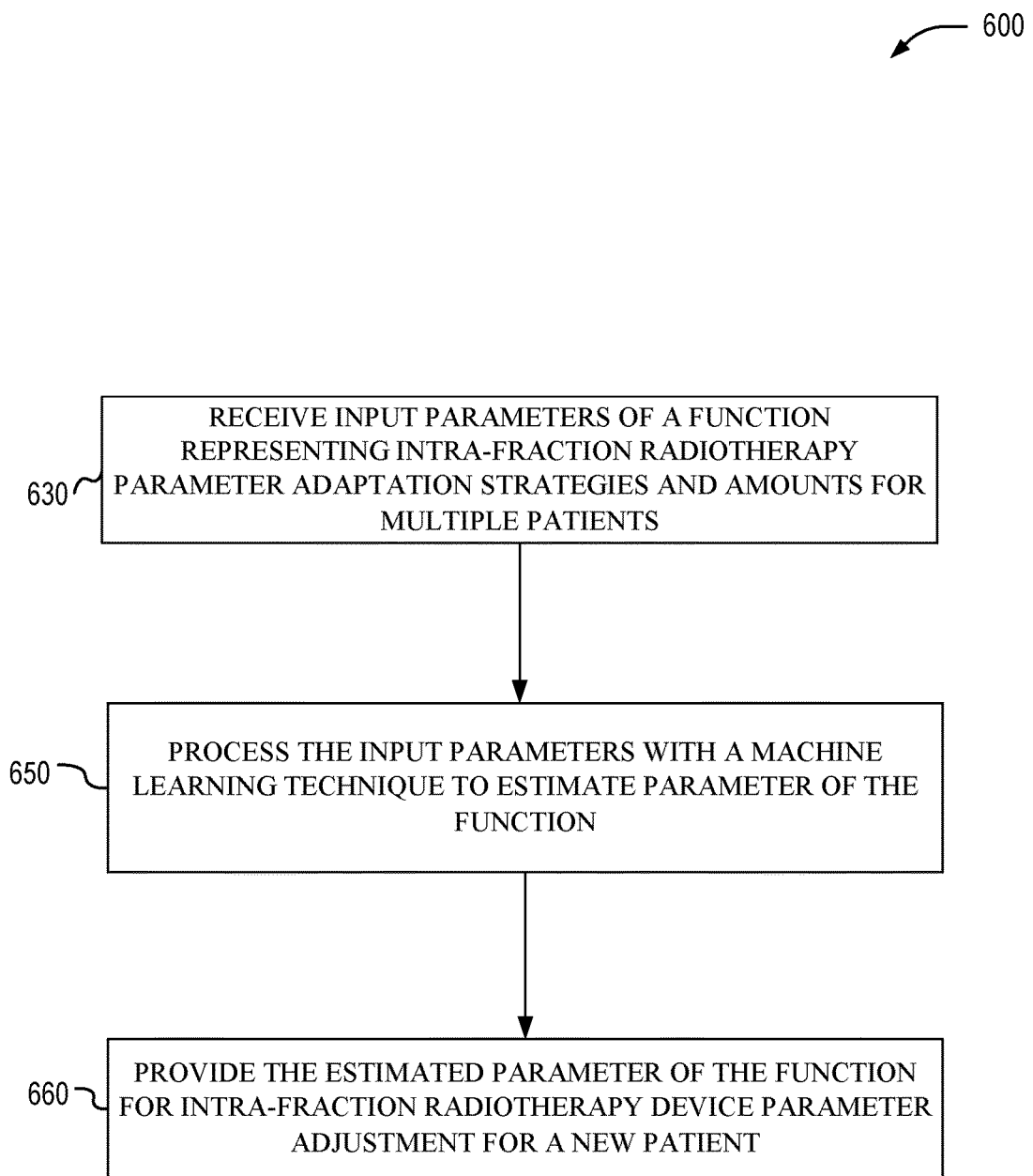

FIG. 6 is a flowchart illustrating example operations of the treatment processing logic 120 in performing process 600, according to example embodiments. The process 600 may be embodied in computer-readable instructions for execution by one or more processors such that the operations of the process 600 may be performed in part or in whole by the functional components of the treatment processing logic 120; accordingly, the process 600 is described below by way of example with reference thereto. However, in other embodiments, at least some of the operations of the process 600 may be deployed on various other hardware configurations. The process 600 is therefore not intended to be limited to the treatment processing logic 120 and can be implemented in whole, or in part, by any other component. Some or all of the operations of process 600 can be in parallel, out of order, or entirely omitted.

At operation 630, treatment processing logic 120 receives input parameters of a function representing intra-fraction radiotherapy parameter adaptation strategies and amounts for multiple patients. For example, the treatment processing logic 120 receives the device training data 320 that include parameters of Equations 2 and 3 for one or more patients or simulations and the treatment information for each of the patients. The paired data may specify relationship pairs of the treatment information of each patient and the corresponding intra-fraction radiotherapy parameter adaptation strategy and/or parameter adjustment amount utilized to treat the given patient. As an example, a training patient anatomy is obtained at a first time within a training radiotherapy treatment fraction after a training radiotherapy treatment dose has been delivered by a radiotherapy device and a deviation is computed between the training patient anatomy at the first time and reference training patient anatomy during the training radiotherapy treatment fraction. The computed deviation, for example, may represent an amount of overlap between a tumor in the training patient and an organ at risk in the training patient and/or distance between a border of a tumor in the training patient and an organ at risk in the training patient. The reference training patient anatomy indicates a prescribed training dose parameter to be delivered within the training radiotherapy treatment fraction.

At operation 650, treatment processing logic 120 processes the input parameters with a machine learning technique to estimate parameters μ of the adaptation of machine settings τ'. For example, the treatment processing logic 120 trains the device adaptation model parameters 312 by minimizing a first loss function based on a training patient input data and the function of Equation 2 or 3 parameters that represent the intra-fraction radiotherapy parameter adaptation strategies for multiple patients. The device adaptation model training 330 may train the device adaptation model parameters 312 by minimizing a second loss function based on a training patient input data and the function of Equation 2 or 3 parameters that represent the intra-fraction radiotherapy parameter adjustment amounts for multiple patients. As an example, the computed deviation is applied to a machine learning model to estimate one or more intra-fraction radiotherapy treatment parameters of a function (e.g., parameters μ of the adaptation of machine settings τ') that provides a radiotherapy device parameter adjustment based on the one or more intra-fraction radiotherapy treatment parameters (e.g., parameters μ) and the machine learning model is trained to establish a relationship between the computed deviation and the one or more intra-fraction radiotherapy treatment parameters.

At operation 660, treatment processing logic 120 provides the estimated parameter of the function for intra-fraction radiotherapy device parameter adjustment for a new patient. For example, the device adaptation model parameters 312 are provided as the trained device parameter adaptation model 360 to apply as parameters of Equations 2 or 3 to perform real-time adjustment of radiotherapy device parameters within a given fraction for a new patient.

As previously discussed, respective electronic computing systems or devices may implement one or more of the methods or functional operations as discussed herein. In one or more embodiments, the radiotherapy processing computing system 110 may be configured, adapted, or used to control or operate the image-guided radiation therapy device 202, perform or implement the training or prediction operations from model 300, operate the trained device adaptation model 360, perform or implement the operations of the flowcharts 400-600, or perform any one or more of the other methodologies discussed herein (e.g., as part of treatment processing logic 120 and workflow 130). In various embodiments, such electronic computing systems or devices operate as standalone devices or may be connected (e.g., networked) to other machines. For instance, such computing systems or devices may operate in the capacity of a server or a client machine in server-client network environment, or as a peer machine in a peer-to-peer (or distributed) network environment. Features of computing systems or devices may be embodied by a personal computer (PC), a tablet PC, a Personal Digital Assistant (PDA), a cellular telephone, a web appliance, or any machine capable of executing instructions (sequential or otherwise) that specify actions to be taken by that machine.

As also indicated above, the functionality discussed above may be implemented by instructions, logic, or other information storage on a machine readable medium. While the machine-readable medium may have been described in various examples with reference to be a single medium, the term "machine-readable medium" may include a single medium or multiple media (e.g., a centralized or distributed database, and/or associated caches and servers) that store the one or more transitory or non-transitory instructions or data structures. The term "machine-readable medium" shall also be taken to include any tangible medium that is capable of storing, encoding or carrying transitory or non-transitory instructions for execution by the machine and that cause the machine to perform any one or more of the methodologies of the present inventive subject matter, or that is capable of storing, encoding or carrying data structures utilized by or associated with such instructions.

The above detailed description includes references to the accompanying drawings, which form a part of the detailed description. The drawings show, by way of illustration but not by way of limitation, specific embodiments in which the inventive subject matter can be practiced. These embodiments are also referred to herein as "examples." Such examples can include elements in addition to those shown or described. However, this disclosure also contemplates examples in which only those elements shown or described are provided. Moreover, the disclosure also contemplates examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the inventive subject matter or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

The present inventive subject matter also relates to a computing system adapted, configured, or operated for performing the operations herein. This system may be specially constructed for the required purposes, or it may comprise a general purpose computer selectively activated or reconfigured by a computer program (e.g., instructions, code, etc.) stored in the computer. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

inventive subject matter. In view of the above, it will be seen that the several objects of the inventive subject matter are achieved and other beneficial results attained. Having described aspects of the inventive subject matter in detail, it will be apparent that modifications and variations are possible without departing from the scope of aspects of the inventive subject matter as defined in the appended claims. As various changes could be made in the above constructions, products, and methods without departing from the scope of aspects of the inventive subject matter, it is intended that all matter contained in the above description and shown in the accompanying drawings shall be interpreted as illustrative and not in a limiting sense.

The examples described herein may be implemented in a variety of embodiments. For example, one embodiment includes a computing device including processing hardware (e.g., a processor or other processing circuitry) and memory hardware (e.g., a storage device or volatile memory) including instructions embodied thereon, such that the instructions which when executed by the processing hardware, cause the computing device to implement, perform, or coordinate the electronic operations for these techniques and system configurations. Another embodiment discussed herein includes a computer program product, such as may be embodied by a machine-readable medium or other storage device, which provides the transitory or non-transitory instructions to implement, perform, or coordinate the electronic operations for these techniques and system configurations. Another embodiment discussed herein includes a method operable on processing hardware of the computing device, to implement, perform, or coordinate the electronic operations for these techniques and system configurations.

In further embodiments, the logic, commands, or transitory or non-transitory instructions that implement aspects of the electronic operations described above, may be provided in a distributed or centralized computing system, including any number of form factors for the computing system such as desktop or notebook personal computers, mobile devices such as tablets, netbooks, and smartphones, client terminals and server-hosted machine instances, and the like. Another embodiment discussed herein includes the incorporation of the techniques discussed herein into other forms, including into other forms of programmed logic, hardware configurations, or specialized components or modules, including an apparatus with respective means to perform the functions of such techniques. The respective algorithms used to implement the functions of such techniques may include a sequence of some or all of the electronic operations described above, or other aspects depicted in the accompanying drawings and detailed description below.

The above description is intended to be illustrative, and not restrictive. For example, the above-described examples (or one or more aspects thereof) may be used in combination with each other. In addition, many modifications may be made to adapt a particular situation or material to the teachings of the present disclosure without departing from its scope. While the dimensions, types of materials and example parameters, functions, and implementations described herein are intended to define the parameters of the inventive subject matter, they are by no means limiting and are exemplary embodiments. Many other embodiments will be apparent to those of skill in the art upon reviewing the above description. The scope of the inventive subject matter should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the inventive subject matter should be determined with reference to the appended claims, along with the full scope of equivalents to which such claims are entitled.

What is claimed is:

1. A method for adjusting radiotherapy treatment for a patient in real-time, the method comprising:
   determining, by processor circuitry, a patient anatomy at a first time within a given radiotherapy treatment fraction after a radiotherapy treatment dose has been delivered by a radiotherapy device;
   retrieving, by the processor circuitry, a reference patient anatomy for the given radiotherapy treatment fraction that indicates a prescribed dose parameter to be delivered within the given radiotherapy treatment fraction;

comparing, by the processor circuitry, the patient anatomy at the first time with the reference patient anatomy during the given radiotherapy treatment fraction, the comparing comprising:
  determining a first amount of overlap between a tumor in the patient and an organ at risk, laterally or in depth, based on the determined patient anatomy at the first time, the first amount of overlap indicating a first quantity of radiation exposure to the tumor relative to the organ at risk; and
  determining a reference amount of overlap between the tumor in the patient and the organ at risk laterally or in depth based on the reference patient anatomy, the reference amount of overlap indicating a reference quantity of radiation exposure to the tumor relative to the organ at risk; and
based on the comparison of the patient anatomy at the first time with the reference patient anatomy, adjusting, by the processor circuitry, a parameter of the radiotherapy device to change an amount of radiotherapy treatment dose delivered at a second time, following the first time, in accordance with the prescribed dose parameter to be delivered within the given radiotherapy treatment fraction.

2. The method of claim 1, wherein the parameter of the radiotherapy device is adjusted while maintaining the prescribed dose parameter to be delivered within the given radiotherapy treatment fraction, wherein the prescribed dose parameter comprises at least one of a prescribed fraction dose to be delivered to a target within the given radiotherapy treatment fraction, a maximum dose delivered to an organ at risk within the given radiotherapy treatment fraction, or a maximum dose delivered to a relative volume of the organ at risk, further comprising adjusting the parameter of the radiotherapy device throughout the given radiotherapy treatment fraction such that an aggregate amount of radiotherapy treatment dose delivered at multiple times within the given radiotherapy treatment fraction corresponds to the prescribed dose parameter.

3. The method of claim 1 further comprising:
  determining that the first amount is less than the reference amount; and
  increasing the amount of radiotherapy treatment dose delivered at the second time in response to determining that the first amount is less than the reference amount.

4. The method of claim 1 further comprising:
  determining that the first amount is greater than the reference amount; and
  decreasing the amount of radiotherapy treatment dose delivered at the second time in response to determining that the first amount is greater than the reference amount.

5. The method of claim 1 further comprising:
  determining a relationship between the first amount to the reference amount; and
  modifying the amount of radiotherapy treatment dose delivered at the second time as a function of the relationship between the first amount to the reference amount.

6. The method of claim 1 further comprising:
  determining a first distance between a border of a tumor in the patient and an organ at risk based on the determined patient anatomy at the first time;
  determining a second distance between the border of the tumor in the patient and the organ at risk based on the reference patient anatomy; and
  increasing the amount of radiotherapy treatment dose delivered at the second time based on a deviation between the first and second distances.

7. The method of claim 1 further comprising:
  determining a first distance between a border of a tumor in the patient and an organ at risk based on the determined patient anatomy at the first time;
  determining a second distance between the border of the tumor in the patient and the organ at risk based on the reference patient anatomy; and
  decreasing the amount of radiotherapy treatment dose delivered at the second time based on a deviation between the first and second distances.

8. The method of claim 1, wherein the prescribed dose parameter comprises a dose amount in a given time or a gantry rotation speed, and wherein adjusting the parameter of the radiotherapy device comprises:
  generating a dose amount per time factor as a function of a dose amount per time parameter and an amount of overlap parameter representing overlap between a tumor in the patient and an organ at risk; and
  adjusting the dose amount or the gantry rotation speed by the dose amount per time factor.

9. The method of claim 8, wherein the dose amount per time factor and the amount of overlap parameter are optimized during planning before starting the given radiotherapy treatment fraction or during the given radiotherapy treatment fraction.

10. The method of claim 8 further comprising comparing a result of the comparison of the patient anatomy at the first time with the reference patient anatomy with the amount of overlap parameter, wherein the dose amount is increased when the result is greater than the amount of overlap parameter, and wherein the dose is decreased when the result is less than the amount of overlap parameter.

11. The method of claim 10, wherein at least one of multi-leaf collimator (MLC) setting, a jaw collimator setting, the dose amount per time parameter, or the amount of overlap parameter is computed based on solving an optimization problem that balances amount of radiotherapy dose delivery to a tumor and at least one of the amount of radiotherapy dose delivery to an organ at risk or the amount of radiotherapy dose delivery to healthy tissue.

12. The method of claim 1, wherein the parameter of the radiotherapy device comprises a multi-leaf collimator (MLC) and a jaw collimator setting, and wherein adjusting the parameter comprises:
  generating a collimator adjustment amount based on an overlap amount computed as a function of an amount of sparing of dose delivery to normal tissue relative to a dose delivered to a target, the overlap amount representing an overlap between a tumor in the patient and an organ at risk; and
  adjusting the MLC and jaw setting of the radiotherapy device by the collimator adjustment amount.

13. The method of claim 12, wherein adjusting the collimator setting comprises modifying positions of the jaws and leaves of the MLC to change a shape of the collimator opening, the positions being modified based on the collimator adjustment amount, wherein a position of one of the leaves of the MLC is adjusted by a different amount than a position of another one of the leaves of the MLC.

14. The method of claim 1 further comprising:
  computing a level of accuracy of the determined patient anatomy at the first time; and
  modifying the radiotherapy device parameter based on the computed level of accuracy.

15. The method of claim 1 further comprising:
estimating an amount of dose that remains to be delivered within the given radiotherapy treatment fraction, wherein the parameter of the radiotherapy device is adjusted based on the estimated amount of dose that remains to be delivered.

16. The method of claim 15, wherein the radiotherapy treatment dose is delivered to a given region in the patient anatomy at the first time, further comprising:
determining whether the given region in the patient anatomy will be irradiated by the radiotherapy device at another time within the given radiotherapy treatment fraction; and
modifying the amount of radiotherapy treatment dose delivered at the second time as a function of the determination of whether the given region in the patient anatomy will be irradiated by the radiotherapy device at another time within the given radiotherapy treatment fraction.

17. The method of claim 16 further comprising modifying the amount based on whether the another time is closer to a start of the radiotherapy treatment fraction or an end of the given radiotherapy treatment fraction.

18. The method of claim 1 further comprising re-ordering segments in a radiotherapy treatment plan to change times when different regions of the patient anatomy are irradiated within the given radiotherapy treatment fraction, wherein:
the radiotherapy treatment plan identifies a first region of the patient anatomy to irradiate at a third time within the given radiotherapy treatment fraction and a second region of the patient anatomy to irradiate at a fourth time within the given radiotherapy treatment fraction; and
after re-ordering the segments, the radiotherapy device irradiates the first region of the patient anatomy at the fourth time within the given radiotherapy treatment fraction and the second region of the patient anatomy at the third time within the given radiotherapy treatment fraction.

19. The method of claim 1 further comprising adding one or more segments in a radiotherapy treatment plan to perform re-scanning and increase times when one or more regions of the patient anatomy are irradiated within the given radiotherapy treatment fraction or to irradiate regions of the patient anatomy that are additional and different from regions specified to be irradiated in the radiotherapy treatment plan.

20. A non-transitory computer readable medium comprising non-transitory computer-readable instructions, the computer-readable instructions comprising instructions for performing operations comprising:
determining a patient anatomy at a first time within a given radiotherapy treatment fraction after a radiotherapy treatment dose has been delivered by a radiotherapy device;
retrieving a reference patient anatomy for the given radiotherapy treatment fraction that indicates a prescribed dose parameter to be delivered within the given radiotherapy treatment fraction;
comparing the patient anatomy at the first time with the reference patient anatomy during the given radiotherapy treatment fraction, the comparing comprising:
determining a first amount of overlap between a tumor in the patient and an organ at risk, laterally or in depth, based on the determined patient anatomy at the first time, the first amount of overlap indicating a first quantity of radiation exposure to the tumor relative to the organ at risk; and
determining a reference amount of overlap between the tumor in the patient and the organ at risk laterally or in depth based on the reference patient anatomy, the reference amount of overlap indicating a reference quantity of radiation exposure to the tumor relative to the organ at risk; and
based on the comparison of the patient anatomy at the first time with the reference patient anatomy, adjusting a parameter of the radiotherapy device to change an amount of radiotherapy treatment dose delivered at a second time, following the first time, in accordance with the prescribed dose parameter to be delivered within the given radiotherapy treatment fraction.

21. The non-transitory computer readable medium of claim 20, wherein the operations further comprise estimating an amount of dose that remains to be delivered within the given radiotherapy treatment fraction, wherein the parameter of the radiotherapy device is adjusted based on the estimated amount of dose that remains to be delivered.

22. The non-transitory computer readable medium of claim 20, wherein the operations further comprise:
re-ordering segments in a radiotherapy treatment plan to change times when different regions of the patient anatomy are irradiated within the given radiotherapy treatment fraction, wherein:
the radiotherapy treatment plan identifies a first region of the patient anatomy to irradiate at a third time within the given radiotherapy treatment fraction and a second region of the patient anatomy to irradiate at a fourth time within the given radiotherapy treatment fraction; and
after re-ordering the segments, the radiotherapy device irradiates the first region of the patient anatomy at the fourth time within the given radiotherapy treatment fraction and the second region of the patient anatomy at the third time within the given radiotherapy treatment fraction.

23. The non-transitory computer readable medium of claim 20, wherein the operations further comprise:
determining that the first amount is less than the reference amount; and
increasing the amount of radiotherapy treatment dose delivered at the second time in response to determining that the first amount is less than the reference amount.

24. The non-transitory computer readable medium of claim 20, wherein the operations further comprise:
determining that the first amount is greater than the reference amount; and
decreasing the amount of radiotherapy treatment dose delivered at the second time in response to determining that the first amount is greater than the reference amount.

25. A system comprising:
a memory for storing instructions; and
one or more processors for executing the instructions stored in the memory for performing operations comprising:
determining a patient anatomy at a first time within a given radiotherapy treatment fraction after a radiotherapy treatment dose has been delivered by a radiotherapy device;
retrieving a reference patient anatomy for the given radiotherapy treatment fraction that indicates a prescribed dose parameter to be delivered within the given radiotherapy treatment fraction;

comparing the patient anatomy at the first time with the reference patient anatomy during the given radiotherapy treatment fraction, the comparing comprising:
determining a first amount of overlap between a tumor in the patient and an organ at risk, laterally or in depth, based on the determined patient anatomy at the first time, the first amount of overlap indicating a first quantity of radiation exposure to the tumor relative to the organ at risk; and
determining a reference amount of overlap between the tumor in the patient and the organ at risk laterally or in depth based on the reference patient anatomy, the reference amount of overlap indicating a reference quantity of radiation exposure to the tumor relative to the organ at risk; and based on the comparison of the patient anatomy at the first time with the reference patient anatomy, adjusting a parameter of the radiotherapy device to change an amount of radiotherapy treatment dose delivered at a second time, following the first time, in accordance with the prescribed dose parameter to be delivered within the given radiotherapy treatment fraction.

26. The system of claim 25, wherein the operations further comprise:
re-ordering segments in a radiotherapy treatment plan to change times when different regions of the patient anatomy are irradiated within the given radiotherapy treatment fraction, wherein:
the radiotherapy treatment plan identifies a first region of the patient anatomy to irradiate at a third time within the given radiotherapy treatment fraction and a second region of the patient anatomy to irradiate at a fourth time within the given radiotherapy treatment fraction; and
after re-ordering the segments, the radiotherapy device irradiates the first region of the patient anatomy at the fourth time within the given radiotherapy treatment fraction and the second region of the patient anatomy at the third time within the given radiotherapy treatment fraction.

27. The system of claim 25, wherein the operations further comprise:
determining that the first amount is less than the reference amount; and
increasing the amount of radiotherapy treatment dose delivered at the second time in response to determining that the first amount is less than the reference amount.

28. The system of claim 25, wherein the operations further comprise:
determining that the first amount is greater than the reference amount; and
decreasing the amount of radiotherapy treatment dose delivered at the second time in response to determining that the first amount is greater than the reference amount.

* * * * *

UNITED STATES PATENT AND TRADEMARK OFFICE
CERTIFICATE OF CORRECTION

| | |
|---|---|
| PATENT NO. | : 11,141,609 B2 |
| APPLICATION NO. | : 16/413555 |
| DATED | : October 12, 2021 |
| INVENTOR(S) | : Tilly et al. |

It is certified that error appears in the above-identified patent and that said Letters Patent is hereby corrected as shown below:

On the Title Page

Item [72], delete "Mareks" and insert -- Marcks -- therefor

Signed and Sealed this
Twenty-eighth Day of December, 2021

Drew Hirshfeld
*Performing the Functions and Duties of the
Under Secretary of Commerce for Intellectual Property and
Director of the United States Patent and Trademark Office*